(12) United States Patent
Aker et al.

(10) Patent No.: US 10,081,596 B2
(45) Date of Patent: Sep. 25, 2018

(54) BIS-INDOLYLMETHANES, A PROCESS FOR THEIR PREPARATION AND USES THEREOF

(71) Applicant: Sanko Tekstil Isletmeleri San. Ve Tic. A.S., Inegol-Bursa (TR)

(72) Inventors: Acelya Aker, Esenler-Istanbul (TR); Nuket Ocal, Esenler-Istanbul (TR); Hikmet Nil Ergindemir, Inegol-Bursa (TR); Agamirze Hamitbeyli, Inegol-Bursa (TR)

(73) Assignee: SANKO TEKSTIL ISLETMELERI SAN VE TIC. A.S., Inegol (Bursa) (TR)

( * ) Notice: Subject to any disclaimer, the term of this patent is extended or adjusted under 35 U.S.C. 154(b) by 224 days.

(21) Appl. No.: 15/284,670

(22) Filed: Oct. 4, 2016

(65) Prior Publication Data

US 2017/0096393 A1 Apr. 6, 2017

(30) Foreign Application Priority Data

Oct. 5, 2015 (EP) .................................. 15188403

(51) Int. Cl.
*C07D 209/12* (2006.01)
*D06M 13/325* (2006.01)
*C07D 209/10* (2006.01)
*C07D 209/14* (2006.01)
*A41D 31/00* (2006.01)

(52) U.S. Cl.
CPC .......... *C07D 209/12* (2013.01); *C07D 209/10* (2013.01); *C07D 209/14* (2013.01); *D06M 13/325* (2013.01); *A41D 31/0011* (2013.01); *A41D 31/0077* (2013.01); *A41D 2400/26* (2013.01); *A41D 2400/34* (2013.01); *D06M 2200/00* (2013.01); *D06M 2200/25* (2013.01)

(58) Field of Classification Search
CPC .. C07D 209/12; C07D 209/10; C07D 209/14; D06M 13/325; D06M 2200/00; D06M 2200/25; A41D 31/0011; A41D 31/0077; A41D 2400/26; A41D 2400/34
USPC ......................................................... 548/400
See application file for complete search history.

(56) References Cited

PUBLICATIONS

European Search Report of EP priority application No. 15188403.8 dated Jan. 15, 2016.
Damodiran M et Al:"Regioselective synthesis and biological evaluation of bis(indolyl)methane . . . ", Biorganic & Medicinal Chemistry Letters,Pergamon,vol. 19,No. 13 Jul. 1, 2009.
Sharma D.K. et al:"A new class of bacterial agents against *S. aureus*, MRSA and VRE derived . . . ", Medicinal Chemistry Research,vol. 23,No. 4,Sep. 4, 2013,pp. 1643-1653.

*Primary Examiner* — Kristin A Vajda

(57) ABSTRACT

The present invention relates to novel bis-indolylmethanes, a process for their preparation and their use in the preparation of technical textiles and PPE's (Personal Protective Equipments), namely in the preparation of UV-protective and anti-infective textiles and garments.

18 Claims, 28 Drawing Sheets

¹H NMR Spectrum

UV Spectrum $^{13}$C NMR Spectrum (APT)

1H NMR Spectrum

UV Spectrum

Figure 25

| Number of Specimen | UVA TRANSMITTANCE (315-400 nm) (%) | UVB TRANSMITTANCE (280-315 nm) | ULTRAVIOLET PROTECTION FACTOR (UPF) | UVA BLOCKING (%) | UVB BLOCKING (%) |
|---|---|---|---|---|---|
| 1 | 6.1 | 2.3 | 28.6 | 93.9 | 97.7 |
| 2 | 5.2 | 1.6 | 39.7 | 94.8 | 98.4 |
| 3 | 4.9 | 1.8 | 36.4 | 95.1 | 98.2 |
| 4 | 6.7 | 2.5 | 27.3 | 93.3 | 97.5 |
| 5 | 4.8 | 1.8 | 38.2 | 95.2 | 98.2 |
| 6 | 6.2 | 2.1 | 30.0 | 93.8 | 97.9 |
| AVERAGE | 5.65 | 2.02 | 33.37 | 94.35 | 97.98 |
| STANDARD DEVIATION | 0.79 | 0.34 | 5.36 | 0.79 | 0.34 |

ULTRAVIOLET PROTECTION VALUE for LABEL (According to ASTM D 6603- Unprepared Specimen): 27

Protection Classification

Good UV-protection category: between 15 and 24 UPF Value

Very Good UV-protection category: between 25 and 39 UPF Value

Excellent UV-protection category to UPF Value 40 or greater

Figure 26

| DRY Number of Specimen | UVA TRANSMITTANCE (315-400 nm) | UVB TRANSMITTANCE (280-315 nm) | ULTRAVIOLET PROTECTION FACTOR (UPF) | UVA blocking (%) | UVB blocking (%) |
|---|---|---|---|---|---|
| 1 | 0.2 | 0.1 | 516.0 | 99.8 | 99.9 |
| 2 | 0.2 | 0.1 | 1929.3 | 99.8 | 99.9 |
| 3 | 0.2 | 0.1 | 1379.4 | 99.8 | 99.9 |
| 4 | 0.6 | 0.1 | 735.6 | 99.6 | 99.9 |
| 5 | 0.3 | 0.1 | 1868.5 | 99.7 | 99.9 |
| 6 | 0.3 | 0.1 | 1371.9 | 99.7 | 99.9 |
| AVERAGE: | 0.30 | 0.10 | 1300.12 | 99.7 | 99.9 |
| STANDARD DEVIATION: | 0.15 | 0.00 | 576.87 | 0.15 | 0.00 |
| *ULTRAVIOLET PROTECTION FACTOR FOR LABEL | | | +40 | | |

Protection Classification

Good UV-protection category: between 15 and 24 UPF Value

Very Good UV-protection category: between 25 and 39 UPF Value

Excellent UV-protection category to UPF Value 40 or greater

Figure 27

DRY

| Number of Specimen | UVA TRANSMITTANCE (315-400 nm) | UVB TRANSMITTANCE (280-315 nm) | ULTRAVIOLET PROTECTION FACTOR (UPF) | UVA blocking (%) | UVB blocking (%) |
|---|---|---|---|---|---|
| 1 | 2.0 | 0.2 | 250.6 | 98.0 | 99.8 |
| 2 | 2.2 | 0.2 | 223.4 | 97.8 | 99.8 |
| 3 | 2.3 | 0.2 | 171.1 | 97.7 | 99.8 |
| 4 | 2.2 | 0.2 | 230.1 | 97.8 | 99.8 |
| 5 | 2.1 | 0.2 | 255.1 | 97.9 | 99.8 |
| 6 | 2.1 | 0.3 | 170.3 | 97.9 | 99.7 |
| AVERAGE: | 2.15 | 0.22 | 216.77 | 97.85 | 99.78 |
| STANDARD DEVIATION: | 0.10 | 0.04 | 37.63 | 0.10 | 0.04 |
| *ULTRAVIOLET PROTECTION FACTOR FOR LABEL | | | +40 | | |

Protection Classification

Good UV-protection category: between 15 and 24 UPF Value

Very Good UV-protection category: between 25 and 39 UPF Value

Excellent UV-protection category to UPF Value 40 or greater

Figure 28

| DRY | | | | | |
|---|---|---|---|---|---|
| Number of Specimen | UVA TRANSMITTANCE (315-400 nm) | UVB TRANSMITTANCE (280-315 nm) | ULTRAVIOLET PROTECTION FACTOR (UPF) | UVA blocking (%) | UVB blocking (%) |
| 1 | 3.2 | 0.3 | 166.7 | 96.8 | 99.7 |
| 2 | 3.0 | 0.4 | 157.2 | 97.0 | 99.6 |
| 3 | 3.1 | 0.4 | 153.2 | 96.9 | 99.6 |
| 4 | 2.9 | 0.4 | 140.2 | 97.1 | 99.6 |
| 5 | 3.5 | 0.4 | 128.6 | 96.5 | 99.6 |
| 6 | 3.6 | 0.4 | 130.8 | 96.4 | 99.6 |
| AVERAGE: | 3.22 | 0.38 | 146.12 | 96.79 | 99.62 |
| STANDARD DEVIATION: | 0.28 | 0.04 | 15.32 | 0.29 | 0.04 |
| *ULTRAVIOLET PROTECTION FACTOR FOR LABEL | | | +40 | | |

Protection Classification

Good UV-protection category: between 15 and 24 UPF Value

Very Good UV-protection category: between 25 and 39 UPF Value

Excellent UV-protection category to UPF Value 40 or greater

BIS-INDOLYLMETHANES, A PROCESS FOR THEIR PREPARATION AND USES THEREOF

RELATED APPLICATION

This application is related to and claims priority to European application No. EP 15188403.8 filed Oct. 5, 2015, the contents of which are hereby incorporated by reference as if set forth in their entirety.

TECHNICAL FIELD

The present invention relates to novel bis-indolylmethanes, a process for their preparation and their use in the preparation of technical textiles and PPE's (Personal Protective Equipments), namely in the preparation of UV-protective and anti-infective textiles and garments.

BACKGROUND

Ultraviolet radiation (both UVA and UVB) contribute to sunburn, skin ageing, eye damage and skin cancer. It is therefore commonly acknowledged the importance to avoid excessive exposure to the sun and to protect by applying sunscreens to the skin.

Recently sun-protecting clothing is becoming popular, said clothing being called PPEs (Personal Protective Equipments). In some cases, PPEs are also able to protect the body from infections, creating a barrier between the wearer and germs and are especially useful for health-care or biological laboratory workers. Indeed, PPEs are designed to reduce the exposure to hazards, either being them caused by sun or other UV source exposure or by bacteria, fungi, virus and the like.

There is a need to develop improved fabrics for the manufacture of PPEs which provide a more effective barrier between the wearer and the environment.

BRIEF DESCRIPTION OF THE DRAWINGS

FIGS. 25 to 28 show the results of the UPF test on a non-treated and treated fabrics.

DESCRIPTION OF THE INVENTION

Figure 1:
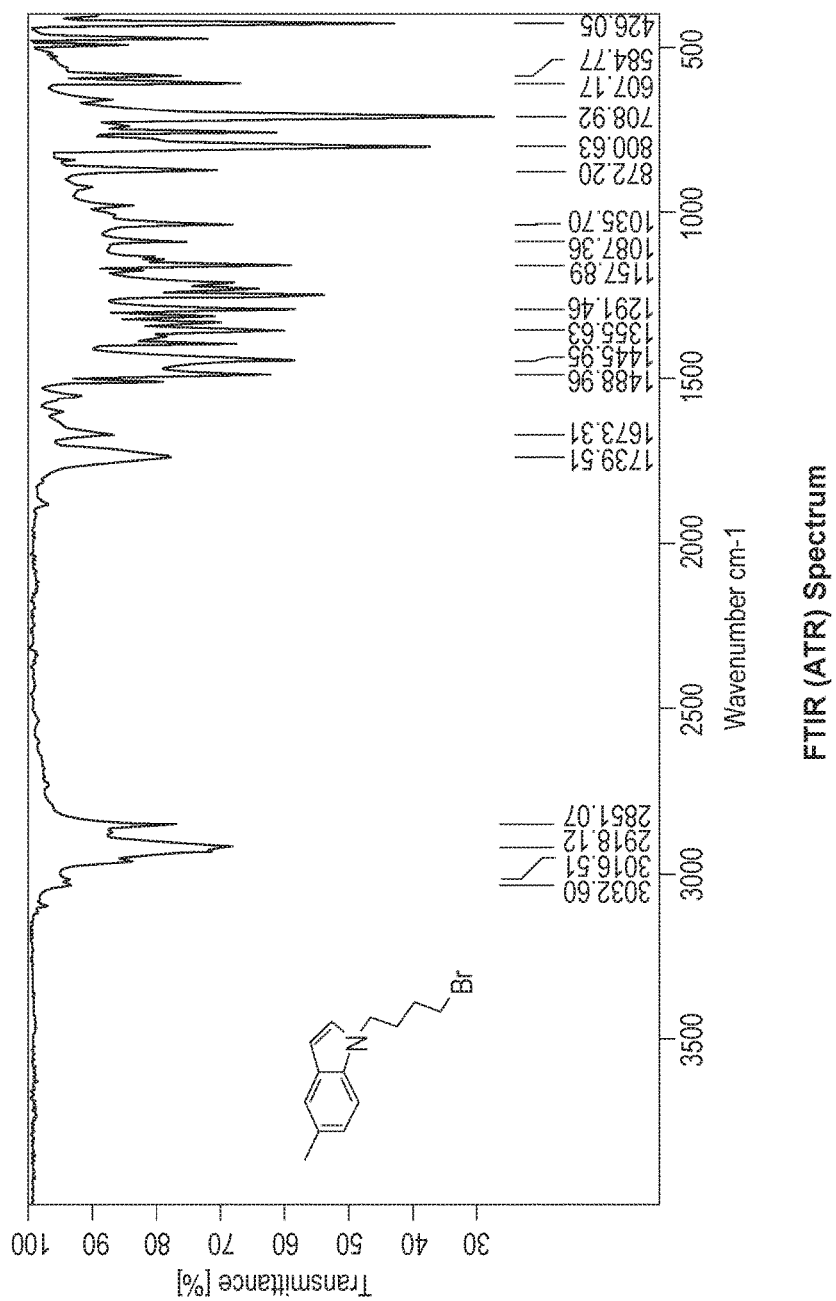
FIGS. 1 to 24 show the analytical data of the compounds of the examples.

It is a scope of the invention to provide new compounds bearing bis-indolyl moiety. It is a further scope of the invention to provide new compounds which are able to impart a textile sun-protective and anti-infective effect. It is a further scope of the invention to provide garments and PPEs which are endowed with sun-protective and anti-infective effect and which are made from the new compounds of the invention. It is another scope of the invention to provide a process for the preparation of the new compounds of the invention.

These and further scopes will be achieved by the subject-matter of the invention, as it will be herein disclosed.

According to one of its aspects, the present invention relates to new compounds of formula (I)

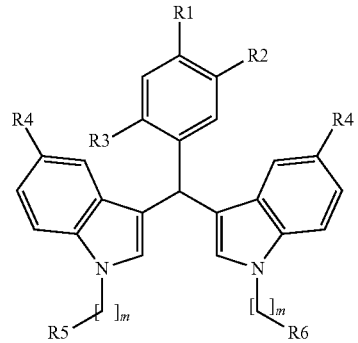

(I)

wherein $R_1$ is selected from hydrogen, a halogen atom, a non-substituted, saturated or unsaturated, linear or branched, acyclic C1-C10 alkyl group; and a non-substituted, saturated or unsaturated, linear or branched, acyclic C1-C10 alkoxy group; when R2 and R3 are H;

$R_2$ is selected from hydrogen, a non-substituted, saturated or unsaturated, linear or branched, acyclic C1-C10 alkyl group, and a non-substituted, saturated or unsaturated, linear or branched, acyclic C1-C10 alkoxy group; when R1 is H and R3 are alkyl or alkoxy groups as above defined;

$R_3$ is selected from hydrogen, a halogen atom, a non-substituted, saturated or unsaturated, linear or branched, acyclic C1-C10 alkyl group, and a non-substituted, saturated or unsaturated, linear or branched, acyclic C1-C10 alkoxy group; when R1 is H and R3 are halogen, alkyl or alkoxy as above defined;

$R_4$ is selected from a non-substituted, saturated or unsaturated, linear or branched, acyclic C1-C10 alkyl group and a non-substituted, saturated or unsaturated, linear or branched, acyclic C1-C10 alkoxy group;

$R_5$ is selected from a halogen atom, polyvinylalcohol; polyvinylamine and a cellulose-polymer;

$R_6$ is selected from a halogen atom; polyvinylalcohol; polyvinylamine and a cellulose-polymer;

m is from 3 to 5.

Preferably the alkyl group is a linear C1-C4 alkyl group. According to a preferred embodiment, the alkyl group is a methyl group. Preferably the alkoxy group is a linear C1-C4 alkoxy group. According to a preferred embodiment, the alkoxy group is a methoxy group.

The term "halogen" here represents chlorine, bromine, iodine and fluorine. Chlorine and bromine are preferred. Polyvinylalcohol herein defines a residue of a polyvinylalcohol, which is bound to the alkyl chain by an oxygen atom. A preferred PVA molecular weight is approx. 100,000-130,000 g/mol with a Pw: 2,700 (polymerisation degree) and hydrolysis ratio: 86-88%. PVA as above is commercially available.

Embodiments include the following:

$R_2$ is hydrogen and $R_1$ and $R_3$ are both halogen, advantageously both chlorine;

$R_1$ is hydrogen and $R_2$ and $R_3$ are both alkoxy groups advantageously both a methoxy group;

$R_2$ and $R_3$ are both hydrogen and $R_1$ is halogen, advantageously fluorine;

$R_4$ are a methyl group;
$R_5$ and $R_6$ are both halogen, advantageously bromine;
$R_5$ is bromine and $R_6$ is polyvinylalcohol;
m is 4.
Particularly preferred are compounds of formula (I) wherein
$R_2$ is hydrogen; $R_1$ and $R_3$ are both chlorine; $R_4$ and $R_5$ are both methyl groups;
$R_5$ and $R_6$ are both bromine; m is 4;
$R_1$ is hydrogen; $R_2$ and $R_3$ are both a methoxy group; $R_4$ is a methyl group; $R_5$ and $R_6$ are both bromine; m is 4;
$R_1$ is fluorine; $R_2$ and $R_3$ are both hydrogen; $R_4$ is a methyl group; $R_5$ and $R_6$ are both bromine; m is 4;
$R_2$ is hydrogen; $R_1$ and $R_3$ are both chlorine; $R_4$ is methyl groups; $R_5$ is bromine and $R_6$ is polyvinylalcol; m is 4;
$R_1$ is hydrogen; $R_2$ and $R_3$ are both a methoxy group; $R_4$ is a methyl group; $R_5$ is bromine and $R_6$ is polyvinylalcol; m is 4;
$R_1$ is fluorine; $R_2$ and $R_3$ are both hydrogen; $R_4$ is a methyl group; $R_5$ is bromine and $R_6$ is polyvinylalcol; m is 4;

The compounds of the invention may be prepared by a process according to the following Scheme ture of the reaction is comprised between room temperature and the reflux temperature of the reaction mixture, preferably between 40 and 80° C., advantageously approx. 50-60° C.

The reaction is complete in few hours, about 1 to 6 hours. The skilled in the art is however able to follow the development of the reaction flow and finishing time, which can be determined, for instance, by using TLC (Thin Layer Chromatography) technique.

Compound of formula (IV) is isolated and, if necessary or desired, purified before being reacted with benzaldehyde of formula (V), preferably in a molar ratio of at least 2/1, in the presence of catalytic amounts of 1,3-dibromo-5,5-dimethylhidantoin (DBDMH). The reaction is preferably carried out without any solvent.

It is advantageous to perform the reaction in an inert environment, such as under nitrogen or argon. The temperature of the reaction is comprised between room temperature and the reflux temperature of the reaction mixture, preferably between 40 and 80° C., advantageously approx. 50-60° C. The reaction is complete in few hours, about 1 to 6 hours.

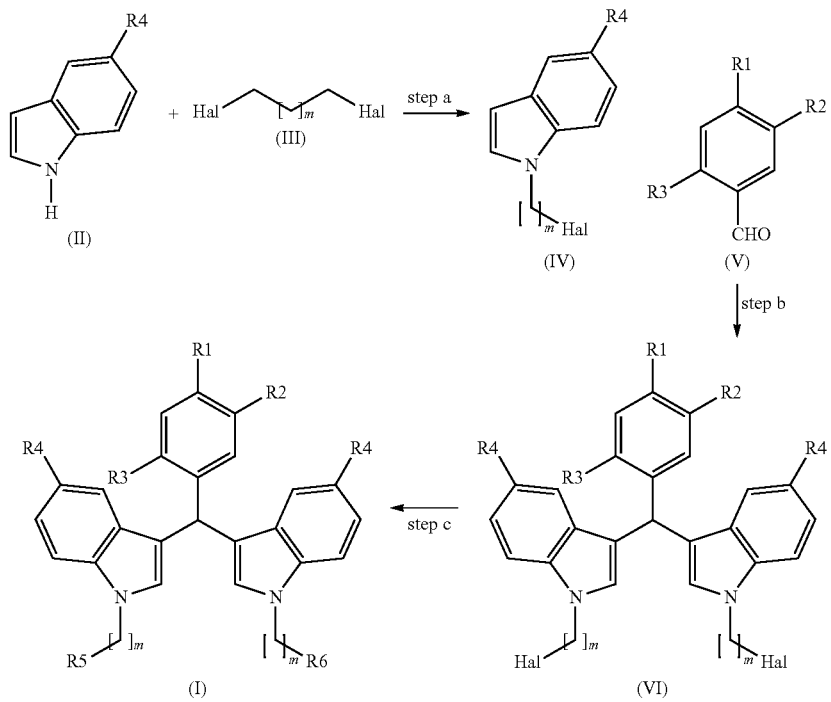

wherein $R_1$, $R_2$, $R_3$, $R_4$, $R_5$, $R_6$ and m are as above defined, Hal is a halogen atom, and m is from 1 to 3.

The above depicted process represents another subject-matter of the invention. Compounds of formula (II) and (III) are known in the art or can be prepared by known methods.

In the process of the invention, a compound of formula (II) is reacted with the dihalo-alkylene (III) in an appropriate solvent, in the presence of a strong base. Preferably, the solvent is selected from an alkanone, such as 2-butanone. However, organic solvents with similar polarity may also be used.

Preferably, the base is a hydroxide, such as an alkali-metal hydroxide, for instance KOH or NaOH. Preferably the molar ratio compound (II)/compound (III)/base is approx. 1/4/2.

It is advantageous to perform the reaction in an inert environment, such as under nitrogen or argon. The tempera- The skilled in the art is however able to follow the development of the reaction by using conventional methods, such as chromatographic techniques.

Compound of formula (VI) is isolated and, if necessary or desired, purified according to the known techniques. Compound (VI) corresponds to compound (I) when $R_6$ is halogen.

To prepare compound (I) wherein $R_6$ is selected from polyvinylalcohol; polyvinylamine and a cellulose-polymer, the following reaction may be carried out.

To a solution of polyvinylalcohol (PVA) or polyvinylamine or a cellulose-polymer, in a suitable solvent, such as dimethylformamide (DMF), in an inert atmosphere and heated at least 100°-120° C., a base, such as potassium carbonate ($K_2CO_3$), is added and the mixture is stirred for a few hours, such as 1 or 2 hours. To that mixture, compound (VI) is added and the reaction is stirred under chromatographic control, such as TLC, for a few hours, such as 2-4 hours. The solvent is evaporated and the desired compound (I) is isolated by filtration. Preferably, the mixture centrifuged before filtering.

Detailed examples of the above reaction are provided in the experimental section of the present description.

Compounds of formula (I) may be used to impart sun-protective and anti-infective effect to textiles. The expression "sun-protective effect" means that the textile and the garments made therewith are able to protect the wearer from UV radiation. The expression "anti-infective effect" means that the textile and the garments are able to protect the body from infections, creating a barrier between the wearer and germs, such as bacteria, especially Gram (+) bacteria and/or fungi and/or virus and/or protozoa and/or helminths.

Indeed, it was found out that coating fabrics with the compounds of the invention increases the UPF (Ultraviolet Protection Factor) label values and, also, confers to the fabric anti-microbial effects, especially anti-bacterial effects, particularly Gram (+) bacteria. This is a valuable technical outcome that allows the treated fabrics to be used in the manufacture of, i.e. PPEs.

The use of compounds of formula (I) in the textile field, in the preparation of sun-protective and anti-infective fabrics and in the manufacture of PPEs is also a subject-matter of the invention, as well as fabrics, clothing and PPEs treated, especially coated, with the compounds of formula (I).

It is another subject-matter of the invention a method to make fabrics sun-protective and anti-infective fabrics which comprises treating, especially coating, said fabrics with the compounds of formula (I).

These fabrics may be obtained by dissolving the compounds of the invention in a suitable solvent, such as for instance dichloromethane and the solution may be added in to a conventional printing paste and then applied to the fabrics. The terms "treat" or "treating" mean that fabrics or clothing or the like are coated of soaked with the compound of the invention.

These fabrics may be obtained by dissolving the compounds of the invention in a suitable solvent, i.e in a solvent which is able to dissolve compounds of formula (I), such as for instance dichloromethane, and the solution may be added in to a conventional printing paste and then applied to the fabrics.

The flat bed screen method for printing application may be carried out, wherein acrylic and modified polymeric resins, as well as conventional cross-linkers may be used for printing paste. The fabrics may then preferably be cured, for instance at 130° C. for 3-5 minutes.

Any kind of fabrics can be coated with the compounds of the invention, including woven, knotted and non-woven fabrics. Preferably, the fabrics are cotton fabrics, advantageously a 100% cotton fabrics. The fabrics may also be denim.

In order to determine if the UV radiation blocked or transmitted by textile fabrics, the known method AATCC 183 was followed. Details of the method are given in the experimental section of the description.

As it can be seen in the experimental section, fabrics treated with the compounds of the invention showed surprisingly high UPFs, all of them being well above the UPF value limit to be included in the "Excellent UV-protection category", i.e. UPF 40.

In order to determine if the antimicrobic activity of the textile fabrics, Washing Standart: BS EN ISO 6330 5A and Antibacterial Test Standart: AATCC 147:2011 were followed. Details of the method are given in the experimental section of the description.

EXPERIMENTAL SECTION

Analytical Spectra of the synthesized compounds are given in the figures enclosed.

Example 1

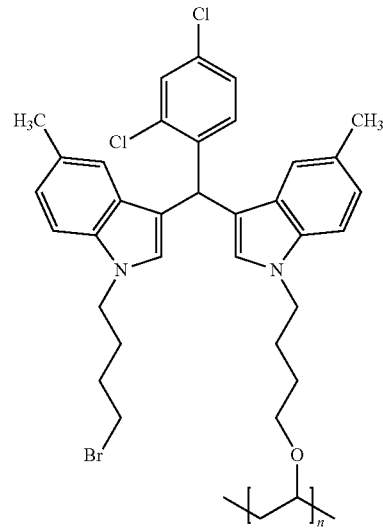

5-methylindole and 1,4-dibromobutane are reacted in 2-butanone in the presence of KOH (molar ratio 5-methylindole/1,4-dibromobutane/KOH=1/4/2) at 55° C., under $N_2$, for 3 hours. The intermediate compound (IV) is purified by column chromatography using silica gel as solid phase and 1/10: ethyl acetate/n-hexane as the eluent system. The purified intermediate is reacted with 2,4-dichlorobenzaldehyde (2/1 molar ratio) in the presence of catalytic amounts of 1,3-dibromo-5,5-dimetilhidantoin (DBDMH), at 55° C., under $N_2$ atmosphere for 2 hours to obtain the intermediate compound (VI) with 67% yield. The intermediate is purified by column chromatography using silica gel as solid phase and 1/15: ethyl acetate/n-hexane as the eluent system. PVA (molecular weight is approx. 100,000-130,000 g/mol with a Pw: 2,700, hydrolysis ratio: 86-88%) is dissolved in dimethylformamide (DMF)(60 mg/3 mL) at 120° C., under $N_2$ at the reflux temperature. After the addition of 70 mg $K_2CO_3$, the reaction mixture stirred up for 1 hour. Then, the intermediate compound (V) (100 mg/2 mL DMF) is added to the mixture. The reaction ended, with TLC control, in 3 hours. DMF is removed, the reaction mixture is centrifugated and sedimented polymers filtered and dried in a drying oven at 45° C., to yield 47% of the title compound.

Analytical Data
Intermediate Compound

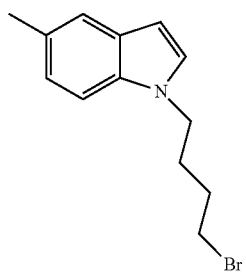

FTIR (ATR): ν=3032 and 3011 (aromatic, =CH streching), 2918 ve 2851 (aliphatic, CH streching), 1673 (C=C streching), 1488, 1445 ve 1355 (aliphatic, intraplanar CH bending) cm−1.

1H NMR (CDCl3, 500 MHz): δ=1.72 (p, J=6.62 Hz, 2H, CH2), 1.88 (p, J=6.9 Hz, 2H, CH2), 2.36 (s, 3H, CH3), 3.25 (t, J=6.62 Hz, 2H, CH2), 4.02 (t, J=6.62 Hz, 2H, CH2), 6.32 (d, J=3.15 Hz, 1H, aromatic), 6.94 (d, J=3.15 Hz, 2H, aromatic), 7.13 (d, J=8.51 Hz, 1H, aromatic), 7.33 (s, 1H, aromatic) ppm. GC-MS (EI, 70 eV): m/z=265 (M+).

Compound

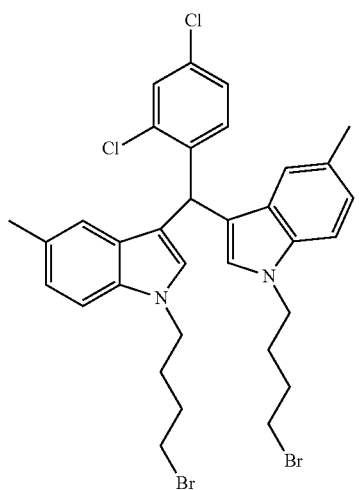 [SMILES: Cc1ccc2c(c1)c(C(c1ccc(Cl)cc1Cl)c1cn(CCCCBr)c3ccc(C)cc13)cn2CCCCBr]

White crystals; m.p.=141–142° C.; $R_f$=0.32 (1:5, ethyl acetate/n-hexane); efficiency: %55

FTIR (ATR): ν=3081 and 3012 (aromatic, =CH streching), 2927, 2874 and 2856 (aliphatic, CH streching), 1585 (C=C streching), 1463 ve 1359 (aliphatic intraplanar, CH bending), 1100 (C—N swing) cm$^{-1}$.

$^1$H NMR (DMSO-$d_6$, 500 MHz): δ=1.64-1.80 (m, 8H, CH$_2$), 2.27 (s, 6H, CH$_3$), 3.47 (t, J=6.62 Hz, 4H, CH$_2$), 4.10 (t, J=6.62 Hz, 4H, CH$_2$), 6.05 (s, 1H, CH), 6.70 (s, 2H, Haromatic), 6.94 (d, J=8.19 Hz, 2H, aromatic), 7.00 (s, 2H, Haromatic), 7.15 (d, J=8.51 Hz, 1H, aromatic), 7.31 (dd, J=2.20; 8.51 Hz, 1H, Haromatic), 7.35 (d, J=8.19 Hz, 2H, Haromatic), 7.63 (s, 1H, Haromatic) ppm.

$^{13}$C NMR (CDCl$_3$, 125 MHz): δ=21.14 (2×CH$_3$), 28.42 (2×CH$_2$), 34.52 (2×CH$_2$), 35.68 (CH), 44.41 (CH$_2$), 109.77 (=CH), 114.75 (Cq), 118.39 (2×CAr), 122.89 (2×CAr), 126.97 (Cq), 127.15 (Cq), 127.25 (CAr), 128.73 (CAr), 131.13 (CAr), 133.60 (Cq), 134.79 (Cq), 140.80 (Cq) ppm.

UV ($λ_{max}$, CH$_2$Cl$_2$):295 nm (c=3.5×10$^{-4}$, A=1.52, ε=4× 10$^{-3}$).

Compound of Example 1

Orange polymer, efficiency: %47

FTIR (ATR): ν=3348 (OH streching), 3026 (aromatic, =CH streching), 2930 ve 2874 (aliphatic CH streching), 1557 ve 1486 (C=C streching), 1367 (aliphatic, intramolecular CH bending), 1165 (C—O streching), 1049 (C—N swing) cm−1.

1H NMR (CDCl3, 500 MHz): 1H NMR (DMSO-d6, 500 MHz): δ=1.41-1.47 (p, 4H, CH2), 1.78-1.84 (p, 4H, CH2), 1.93 (d, J=18.91 Hz, 2H, CH2), 2.32 (s, 6H, CH3), 3.50 (t, J=6.30 Hz, 4H, CH2), 3.97 (t, J=6.62 Hz, 1H, CH), 4.07 (t, J=6.93 Hz, 4H, CH2), 6.15 (s, 1H, CH), 6.53 (s, 2H, aromatic), 6.98 (d, J=8.19 Hz, 2H, aromatic), 7.03 (s, 2H, aromatic), 7.17 (d, J=4.72 Hz, 1H, aromatic), 7.27 (d, J=8.51 Hz, 1H, aromatic), 7.35 (d, J=1.57 Hz, 2H, aromatic) ppm.

UV (λmax, CH2Cl2): 295 nm

Figure 2:
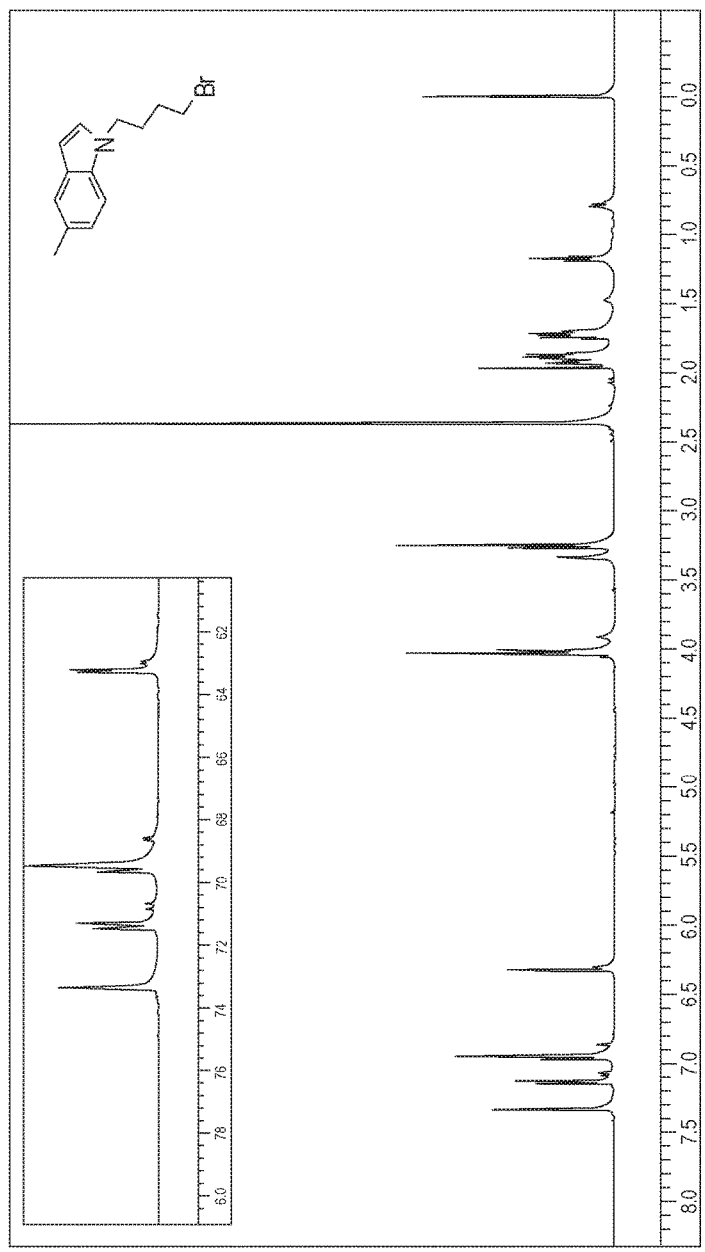
Figure 3:
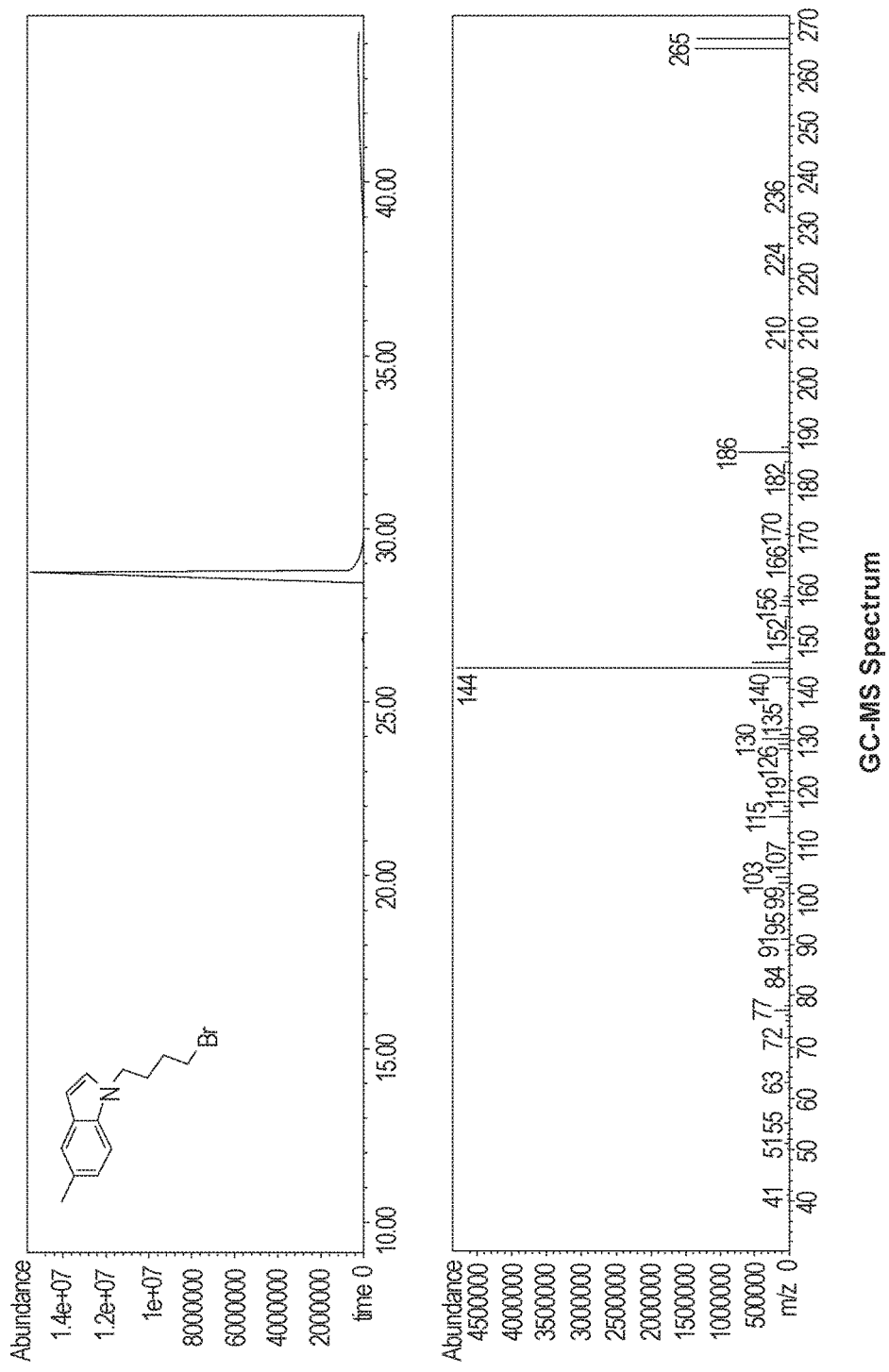
Figure 4:
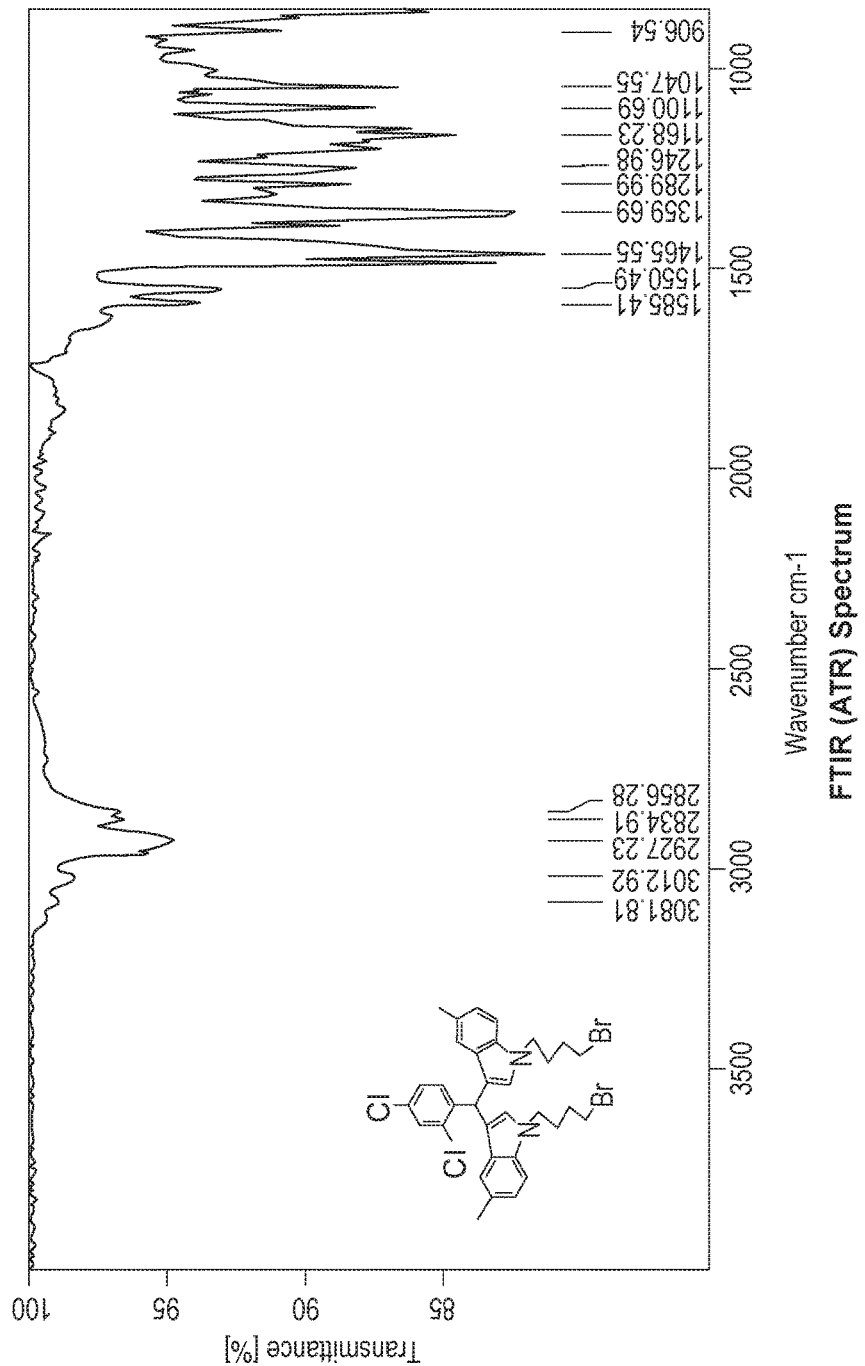
Figure 5:
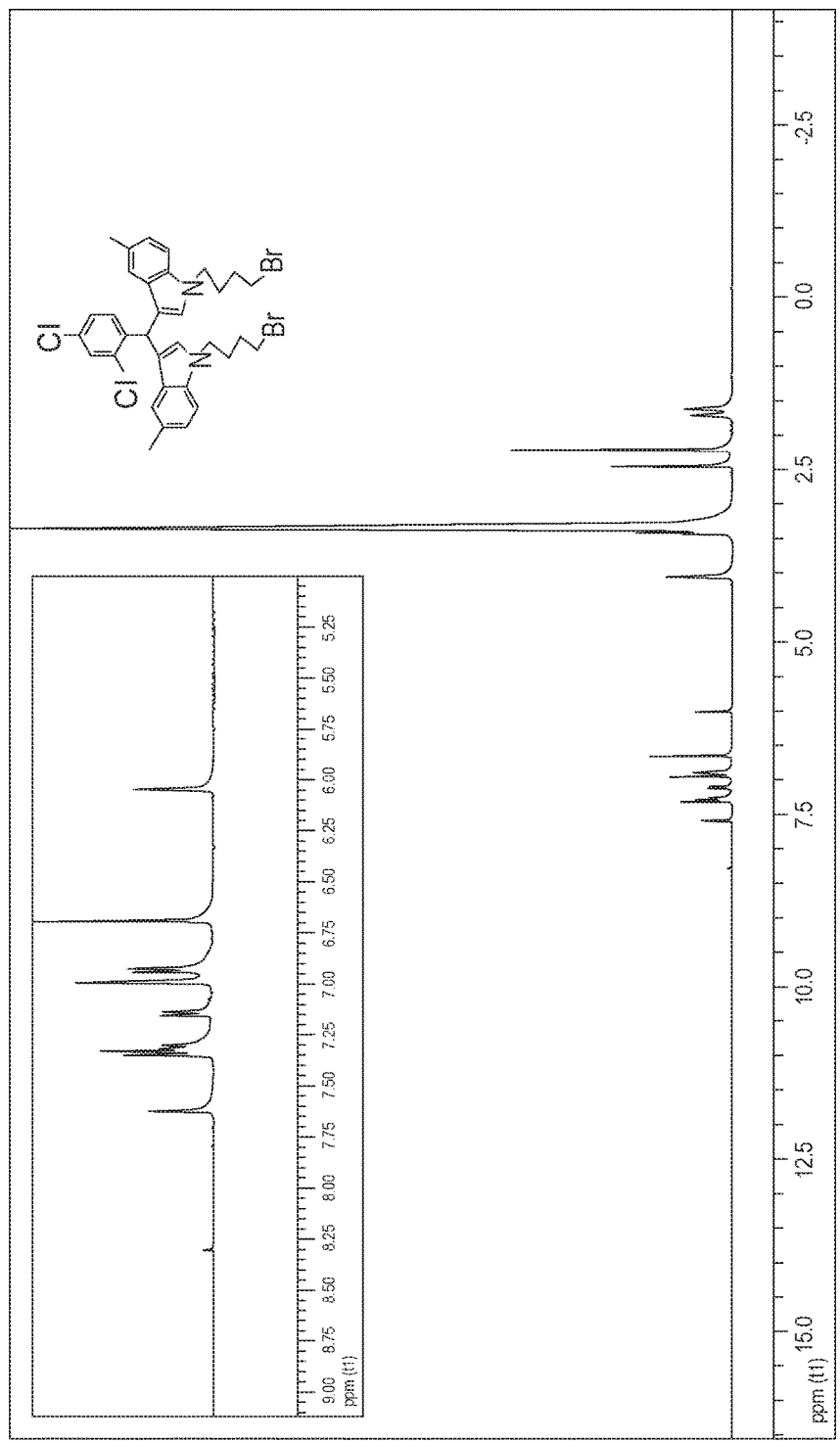
Figure 6:
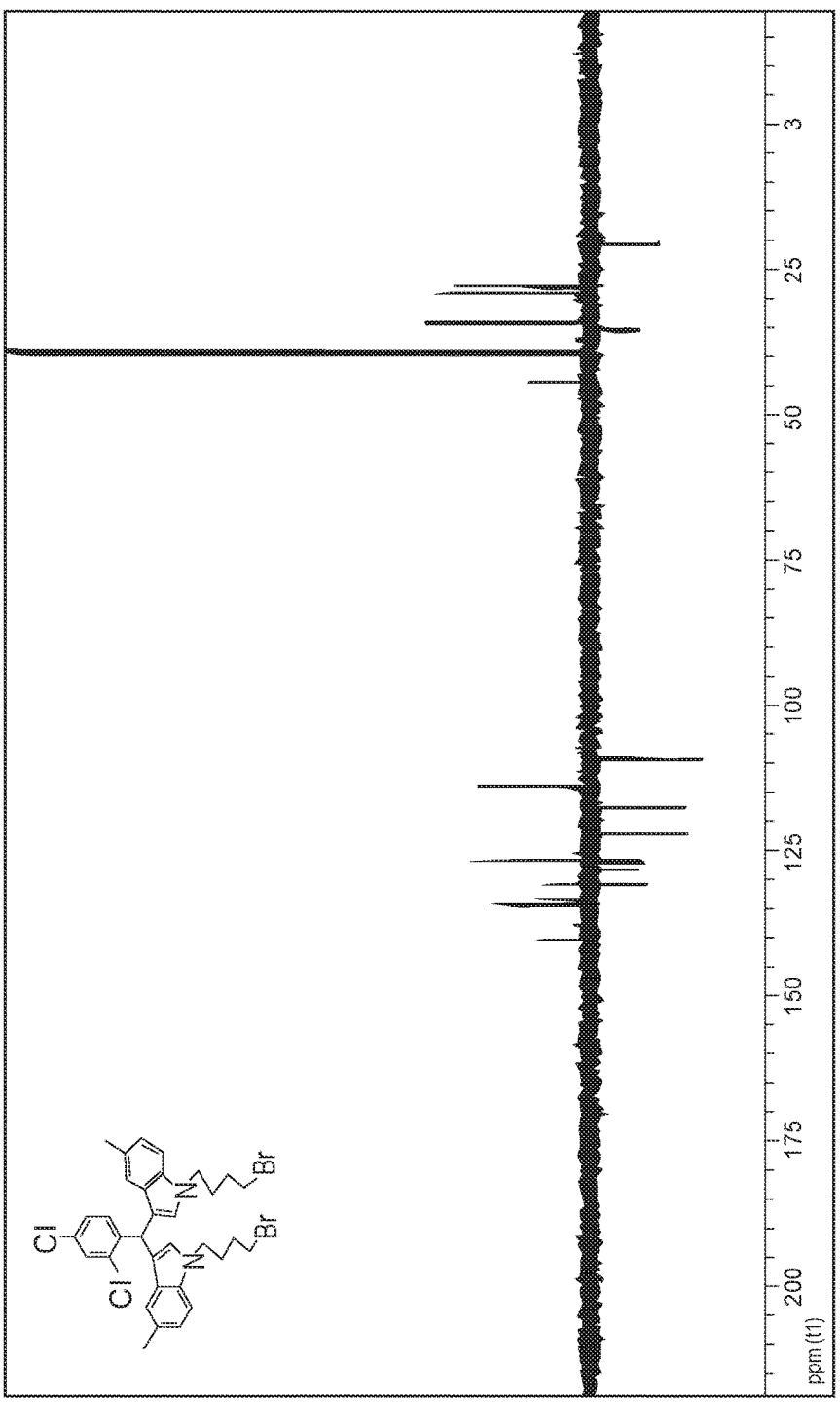
Figure 7:
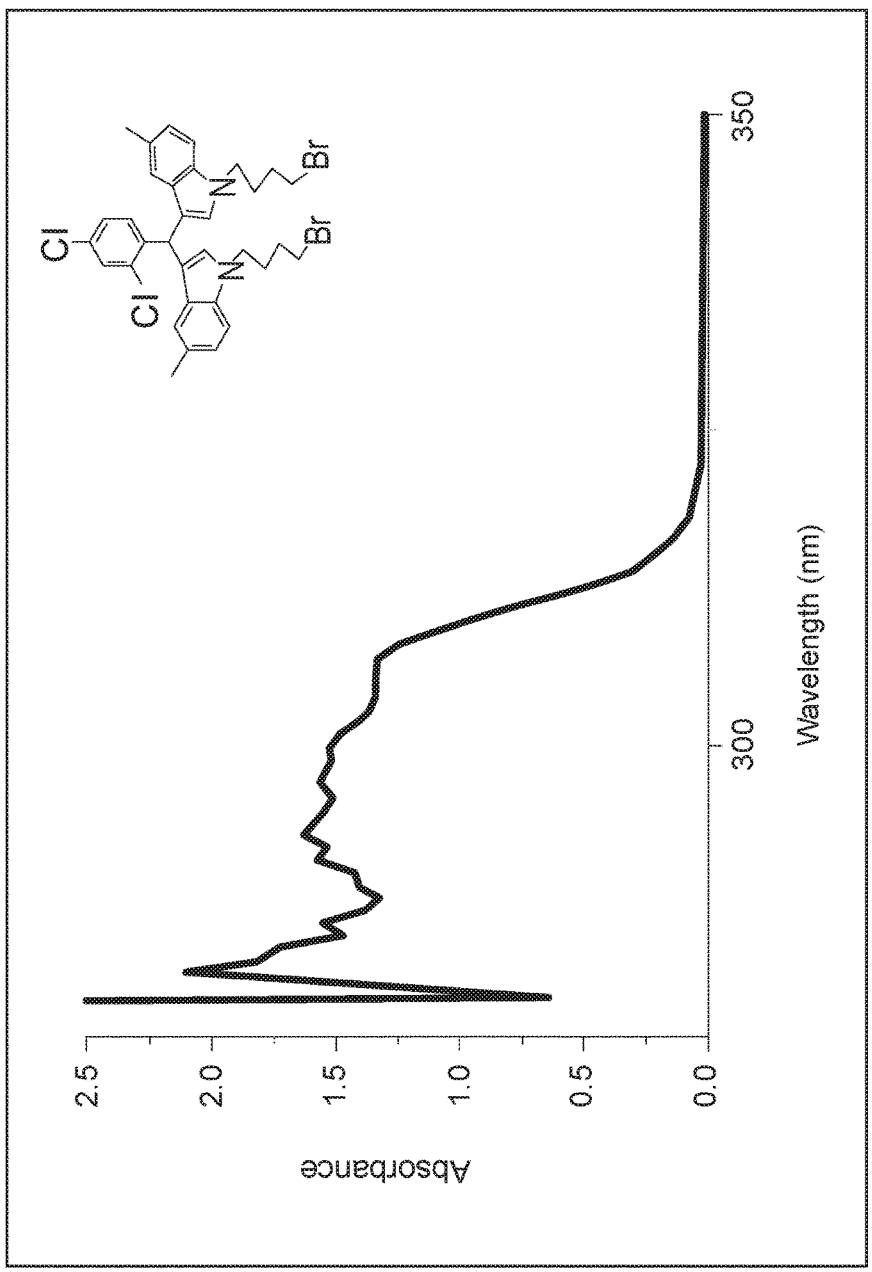
Figure 8:
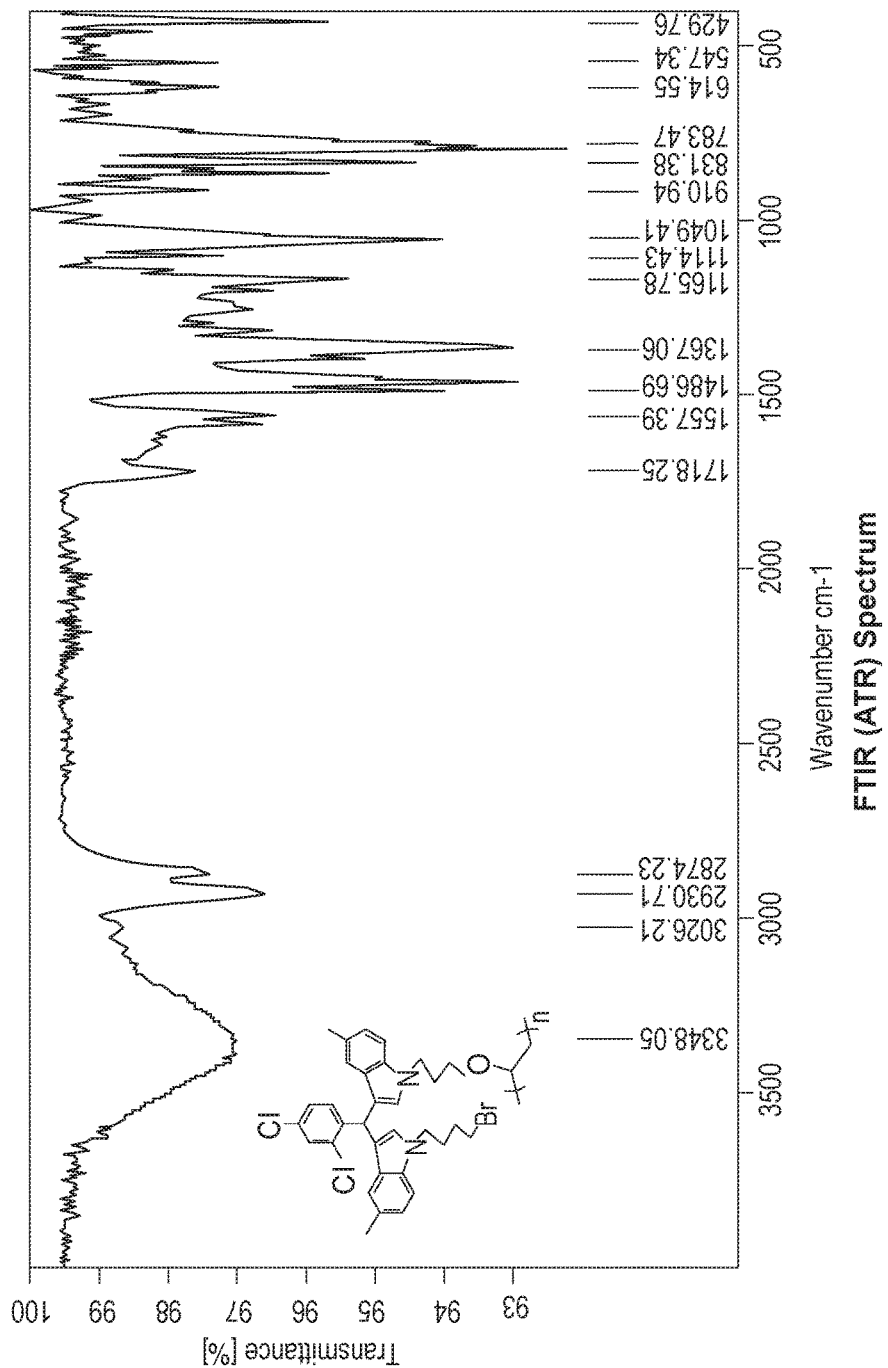
Figure 9:
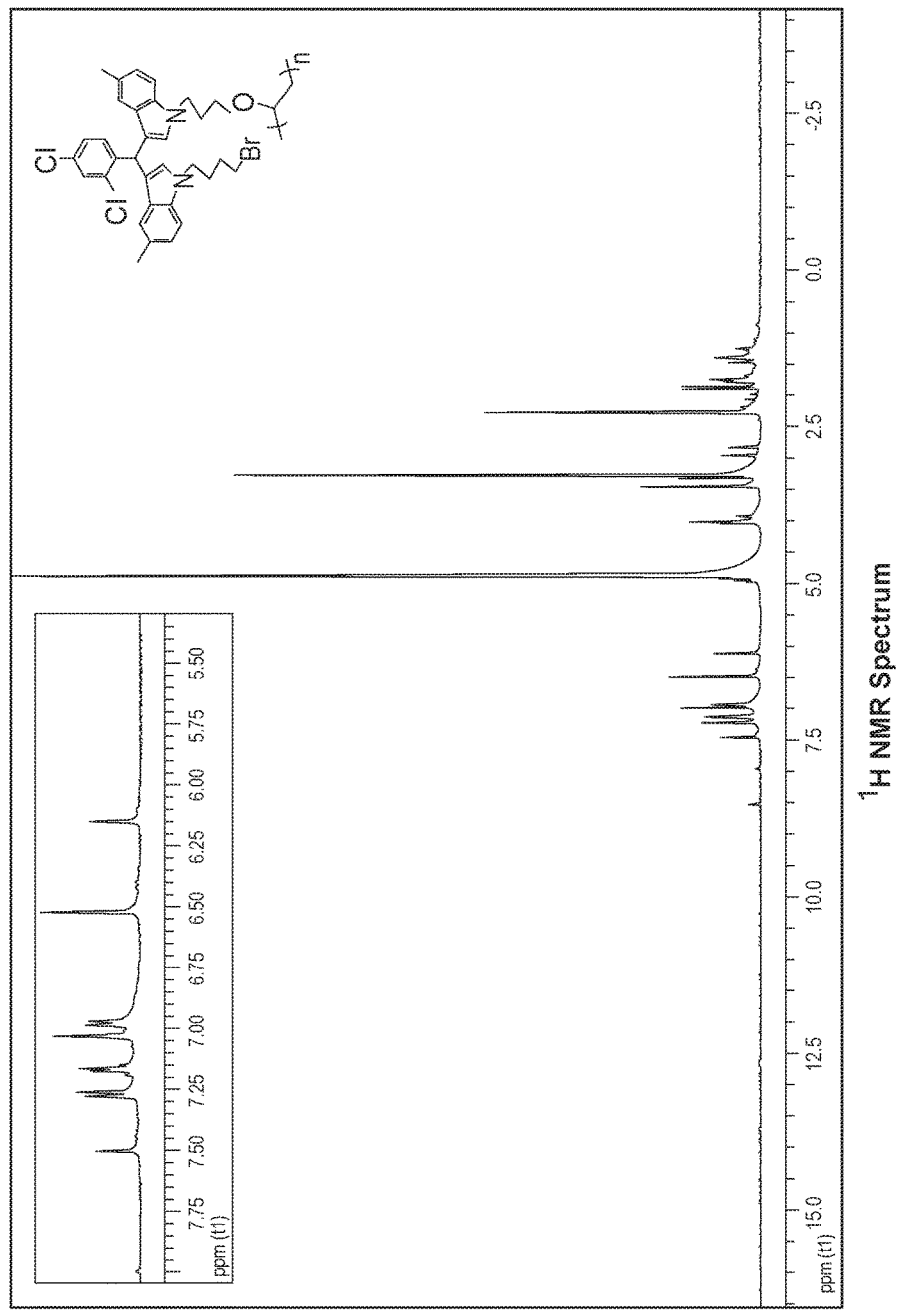
Figure 10:
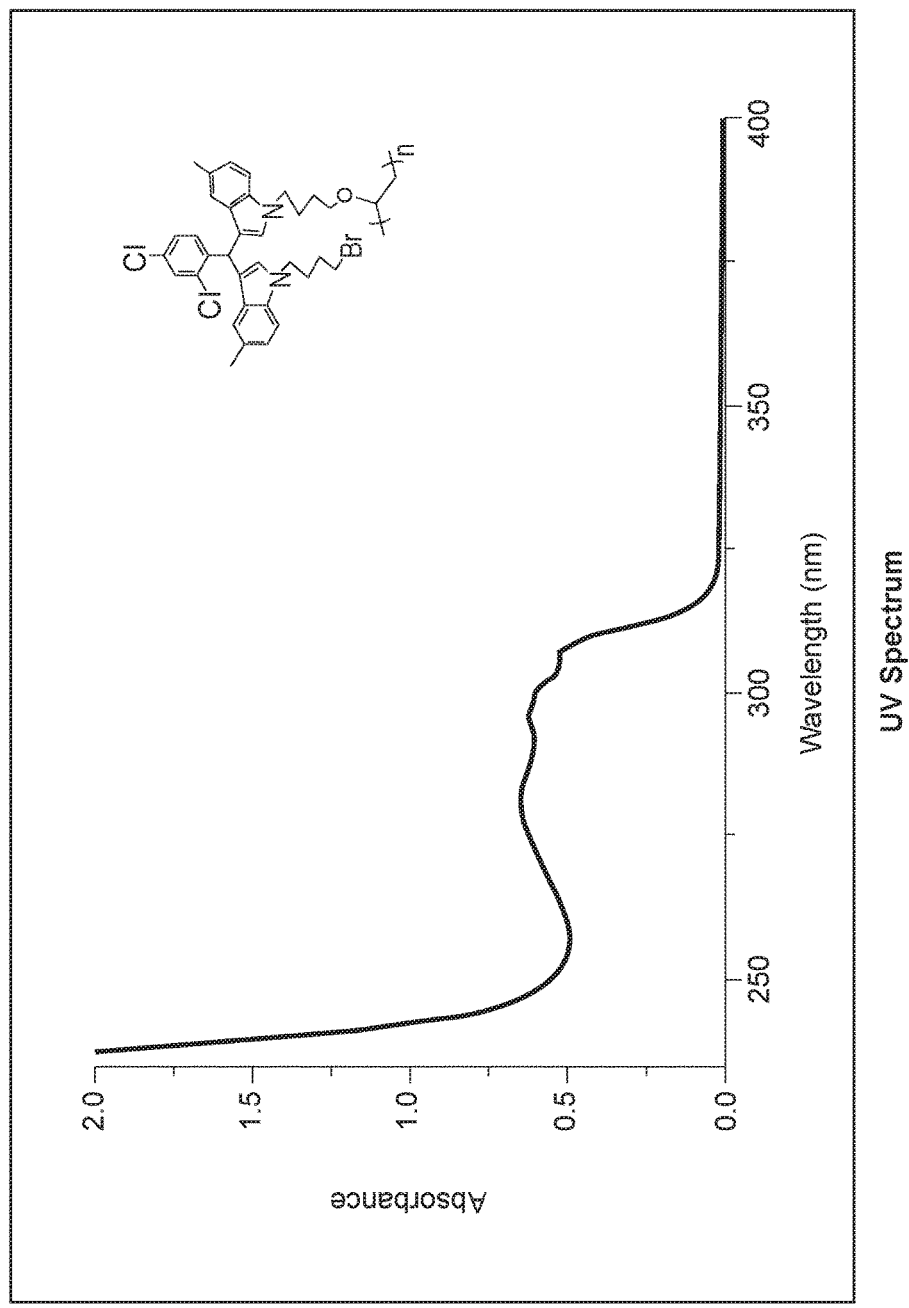

See FIGS. 1 to 10

Example 2

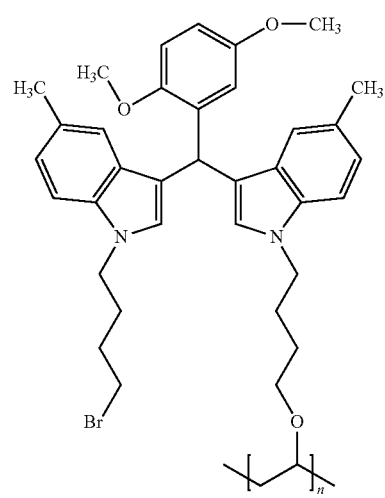

By operating as in Example 1 but using 2,5-dichlorobenzaldehyde instead of 2,4-dichlorobenzaldehyde, the title compound is obtained (yield 49%).

Analytical Data
Compound

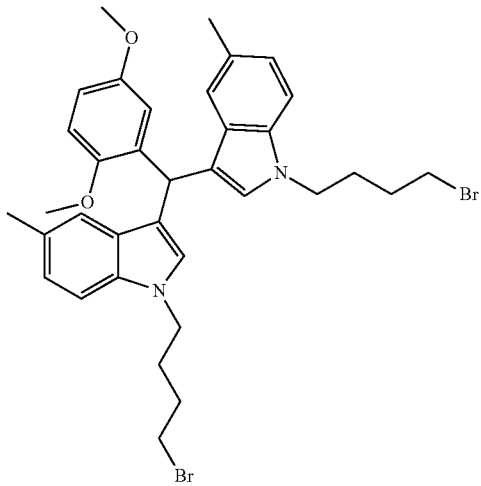 [SMILES: COc1ccc(OC)c(C(c2cn(CCCCBr)c3ccc(C)cc23)c2cn(CCCCBr)c3ccc(C)cc23)c1]

White crystals; m.p.=102° C.; Rf=0.12 (1:15, ethyl acetate/n-hexane); efficiency % 42.

FTIR (ATR):=3022 and 3000 (aromatic, =CH streching), 2939, 2862 and 2831 (aliphatic, CH streching), 1616, 1588 and 1545 (C=C streching), 1489, 1450 and 1363 (aliphatic, intraplanar CH bending), 1024 (C—N swing) cm−1.

1H NMR (DMSO-d6, 500 MHz): δ=1.72-1.76 (p, 4H, CH2), 1.80-1.85 (p, 4H, CH2), 2.32 (s, 6H, CH3), 3.53 (t, J=6.62 Hz, 4H, CH2), 3.62 (s, 3H, OCH3), 3.79 (s, 3H, OCH3), 4.15 (t, J=6.62 Hz, 4H, CH2), 6.13 (s, 1H, CH), 6.66 (d, J=2.83 Hz, 1H, aromatic), 6.76 (s, 2H, aromatic), 6.80 (dd, J=3.15; 8.82 Hz, 1H, aromatic), 6.97 (d, J=8.51 Hz, 2H, aromatic), 7.01 (d, J=8.82 Hz, 1H, aromatic), 7.07 (s, 2H, aromatic), 7.37 (d, J=8.51 Hz, 2H, aromatic), ppm.

13C NMR (CDCl3, 125 MHz): δ=21.5 (2×CH3), 28.8 (2×CH2), 30.0 (2×CH2), 32.1 (CH), 33.1 (2×CH2), 45.3 (2×CH2), 55.5 (CH3), 56.6 (CH3), 108.8 (CAr), 110.6 (CAr), 111.8 (CAr), 116.5 CAr), 117.6 (Cq), 119.9 (CAr), 122.9 (CAr), 127.2 (CAr), 127.7 (Cq), 128.0 (Cq), 134.3 (Cq), 135.0 (Cq), 151.4 (Cq), 153.4 (Cq) ppm.

UV (λmax, CH2Cl2): 285 nm (c=2.4×10−4, A=1.77, ε=7.2×103).

Compound of Example 2

Orange polymer; efficiency % 47

FTIR (ATR): =3372 (OH streching), 3019 (aromatic, =CH streching), 2933 and 2871 (aliphatic, CH streching), 1661, 1589 ve 1547 (C=C streching), 1460 and 1366 (aliphatic intraplanar CH bending), 1211 (C—O streching), 1094 (C—N swing) cm−1.

UV (λmax, CH2Cl2): 295 nm.

Figure 11:
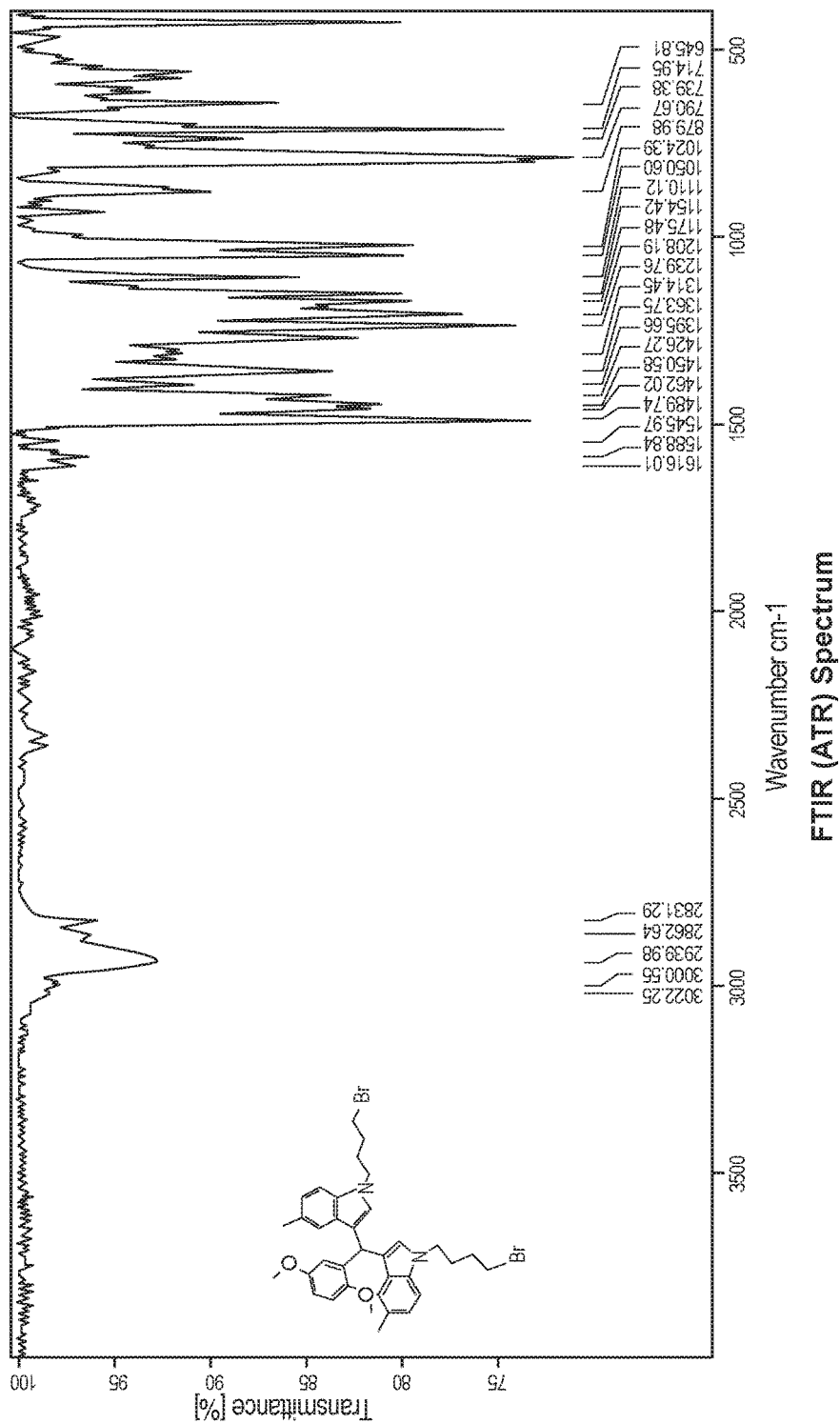
Figure 12:
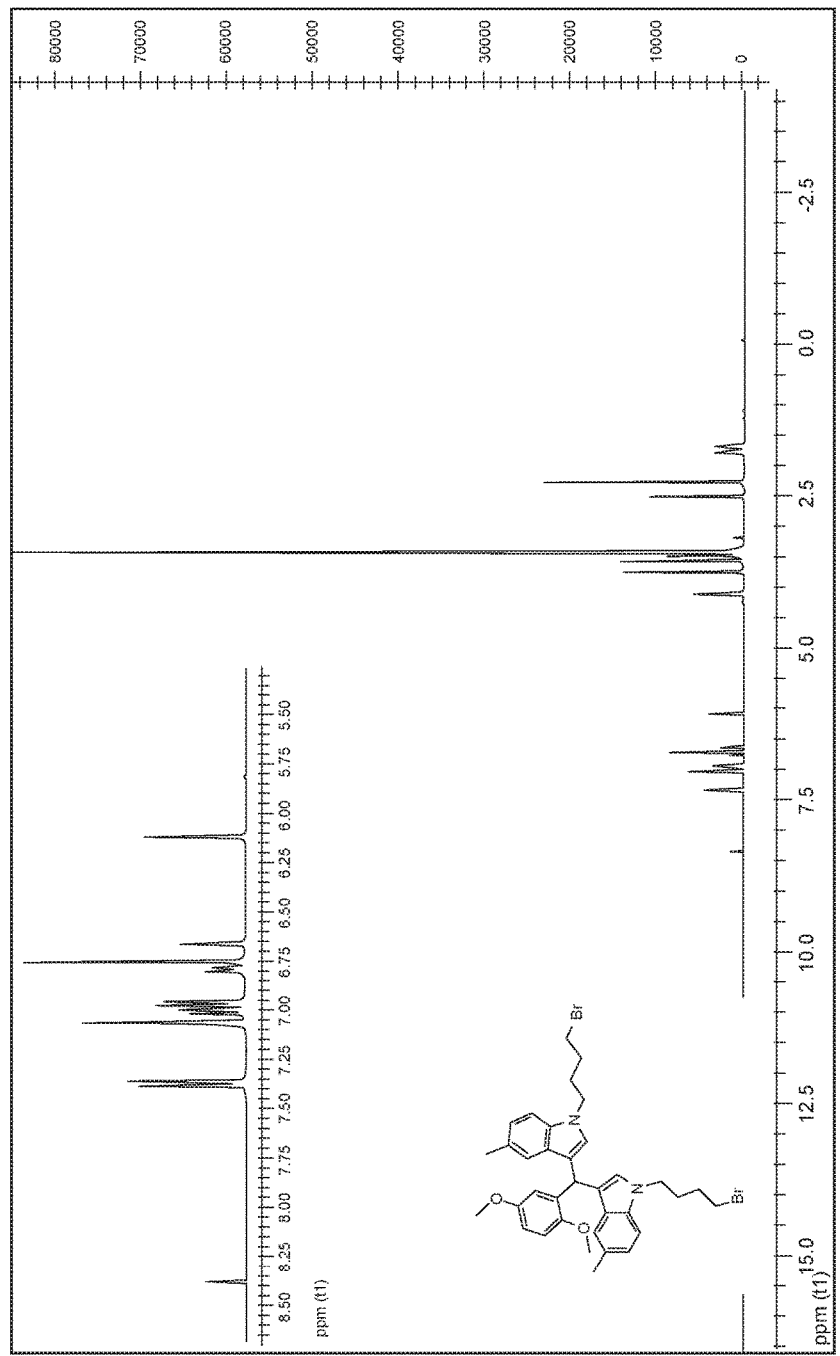
Figure 13:
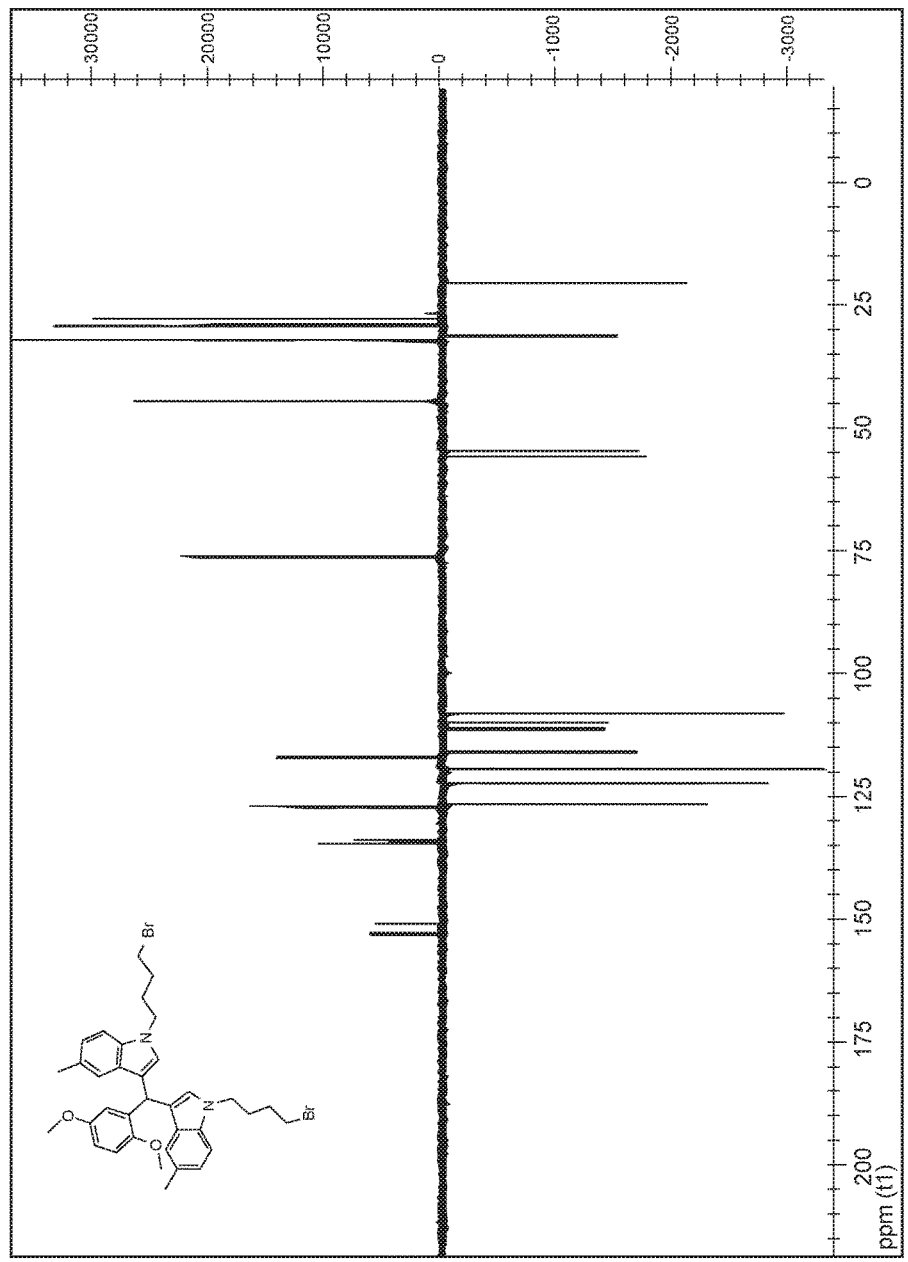
Figure 14:
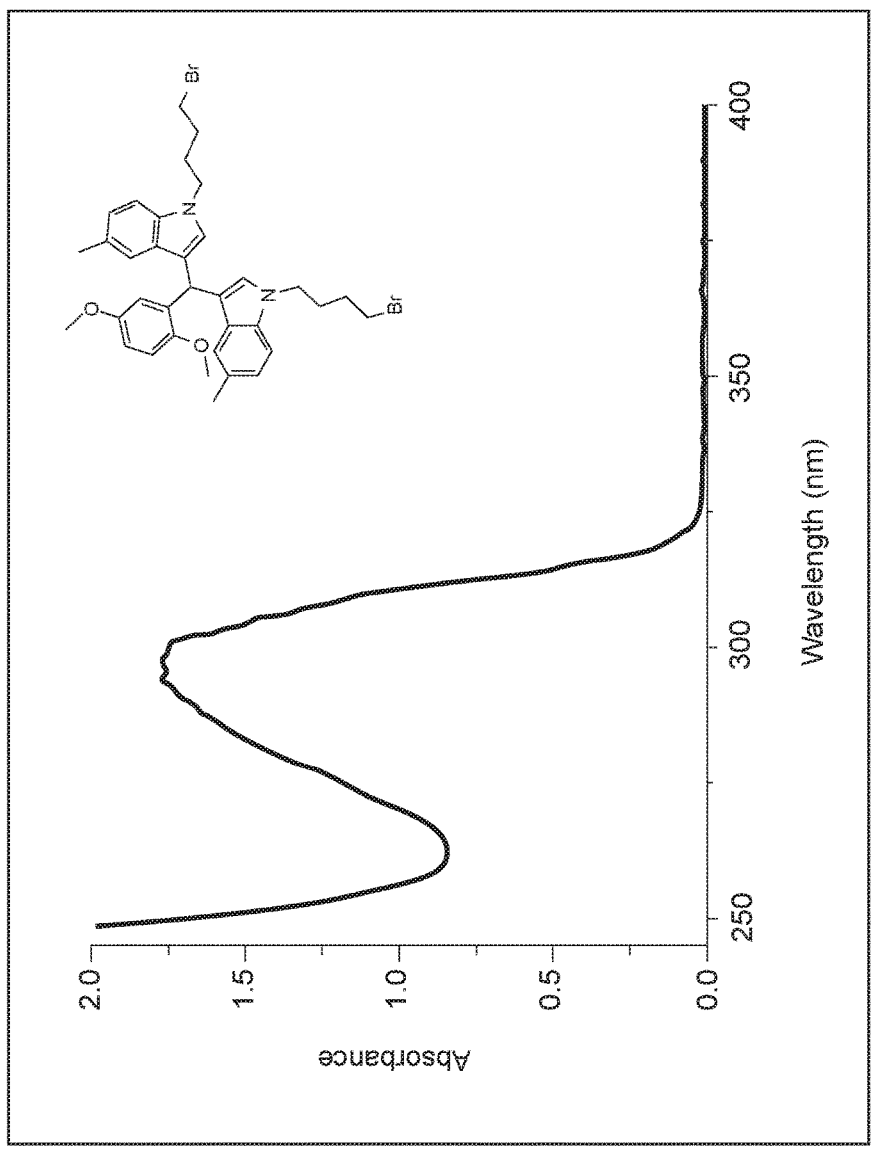
Figure 15:
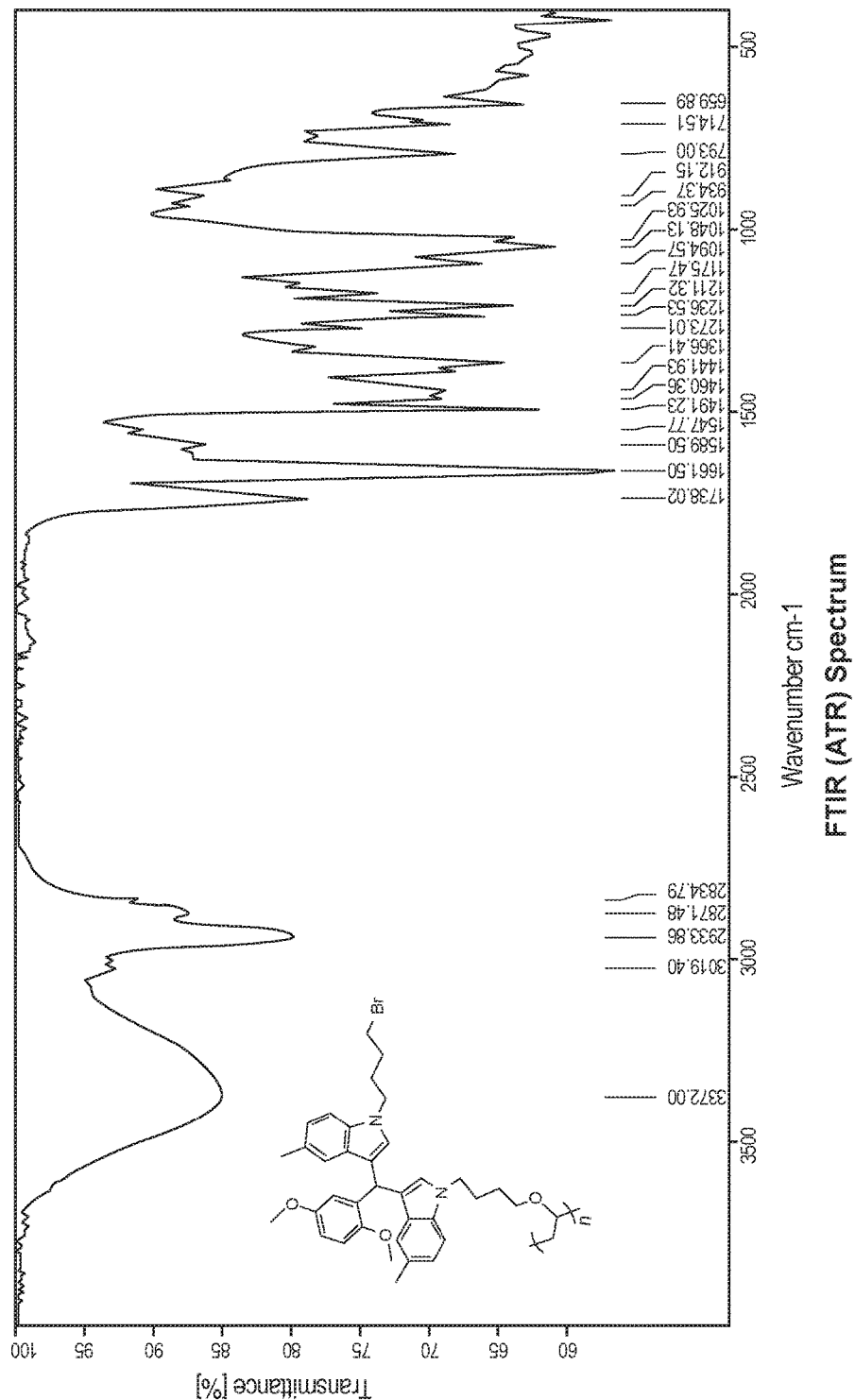
Figure 16:
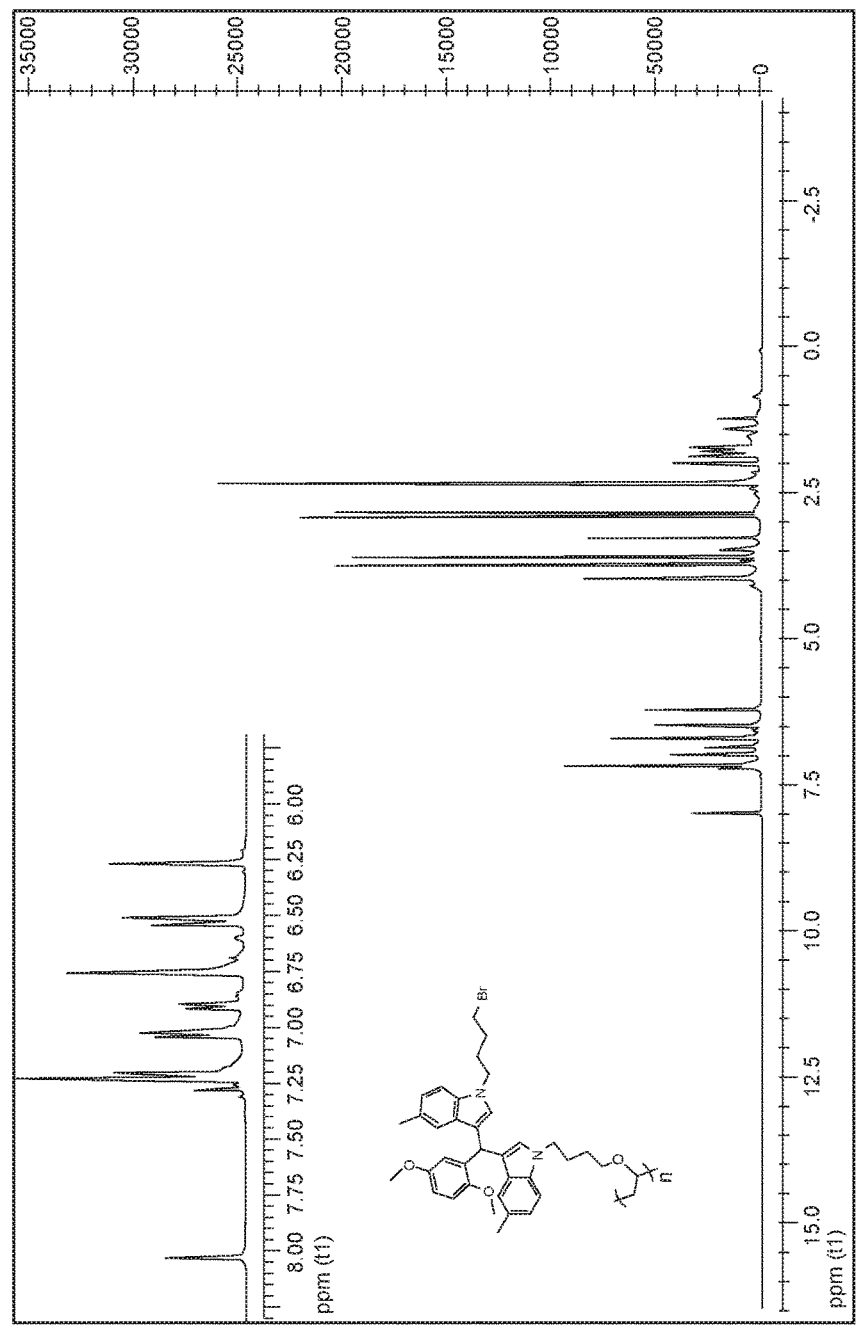
Figure 17:
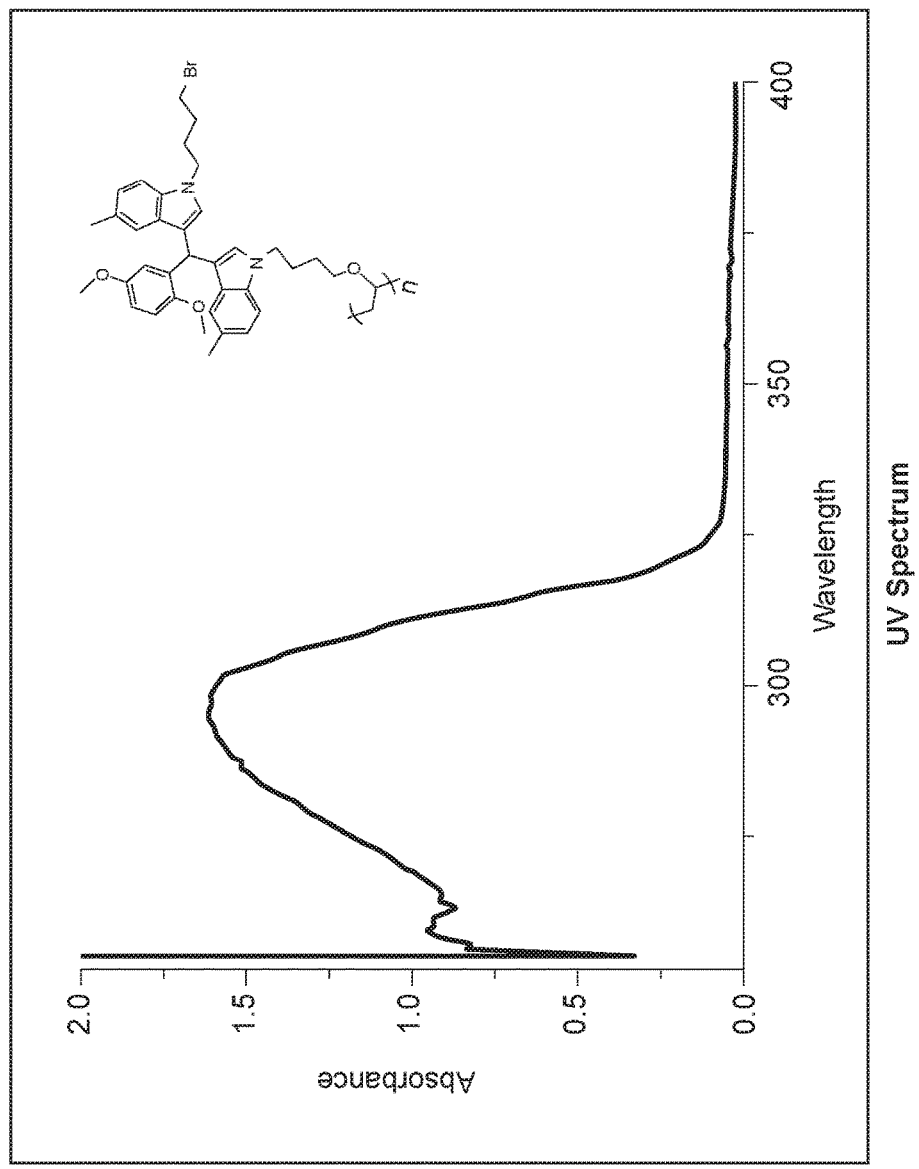

See FIGS. 11 to 17

Example 3

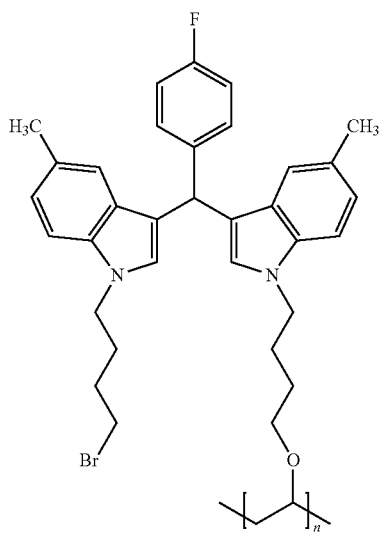

By operating as in Example 1 but using 4-fluorobenzaldehyde instead of 2,4-dichlorobenzaldehyde, the title compound is obtained (yield 45%).

Analytical Data
Compound

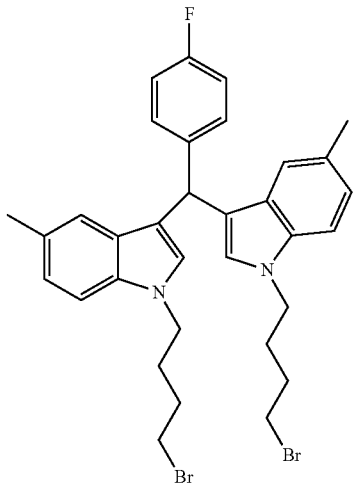 [SMILES: Cc1ccc2c(c1)c(C(c1ccc(F)cc1)c1cn(CCCCBr)c3ccc(C)cc13)cn2CCCCBr]

White crystals; m.p.=118-119 o C; Rf=0.22 (1:15, ethyl acetate/n-hexane); efficiency % 67.

FTIR (ATR): =3028 ve 3009 (aromatic =CH streching), 2957, 2920 and 2854 (aliphatik, CH streching), 1602, 1549 and 1504 (C=C streching), 1485, 1453 and 1359 (aliphatick intraplanar CH streching), 1012 (C—N swing) cm−1.

1H NMR (DMSO-d6, 500 MHz): δ=1.67-1.71 (p, 4H, CH2), 1.75-1.80 (p, 4H, CH2), 2.27 (s, 6H, CH3), 3.48 (t, J=6.62 Hz, 4H, CH2), 4.10 (t, J=6.62 Hz, 4H, CH2), 5.78 (s, 1H, CH), 6.75 (s, 2H, aromatic), 6.92 (d, J=8.19 Hz, 2H, aromatic), 7.06 (s, 2H, aromatic), 7.10 (d, J=8.82 Hz, 2H, aromatic), 7.31-7.34 (m, 4H, aromatic) ppm.

13C NMR (CDCl3, 125 MHz): δ=21.5 (2×CH3), 28.8 (2×CH2), 30.0 (2×CH2), 32.1 (CH), 33.1 (2×CH2), 45.3 (2×CH2), 55.5 (CH3), 56.6 (CH3), 108.8 (CAr), 110.6 (CAr), 111.8 (CAr), 116.5 CAr), 117.6 (Cq), 119.9 (CAr), 122.9 (CAr), 127.2 (CAr), 127.7 (Cq), 128.0 (Cq), 134.3 (Cq), 135.0 (Cq), 151.4 (Cq), 153.4 (Cq) ppm.

UV (λmax, CH2Cl2): 300 nm (c=2.2×10−4, A=1.42, ε=6.4×103).

Compound of Example 3

Brown polymer; efficiency % 52

FTIR (ATR): =3340 (OH streching), 3043 (aromatic, =CH streching), 2932 and 2855 (aliphatic, CH streching), 1661, 1600 and 1504 (C=C streching), 1485 and 1363 (aliphatic intraplanar CH streching), 1217 (C—O streching), 1091 (C—N swing) cm−1.

UV (λmax, DMSO): 295 nm.

Figure 18:
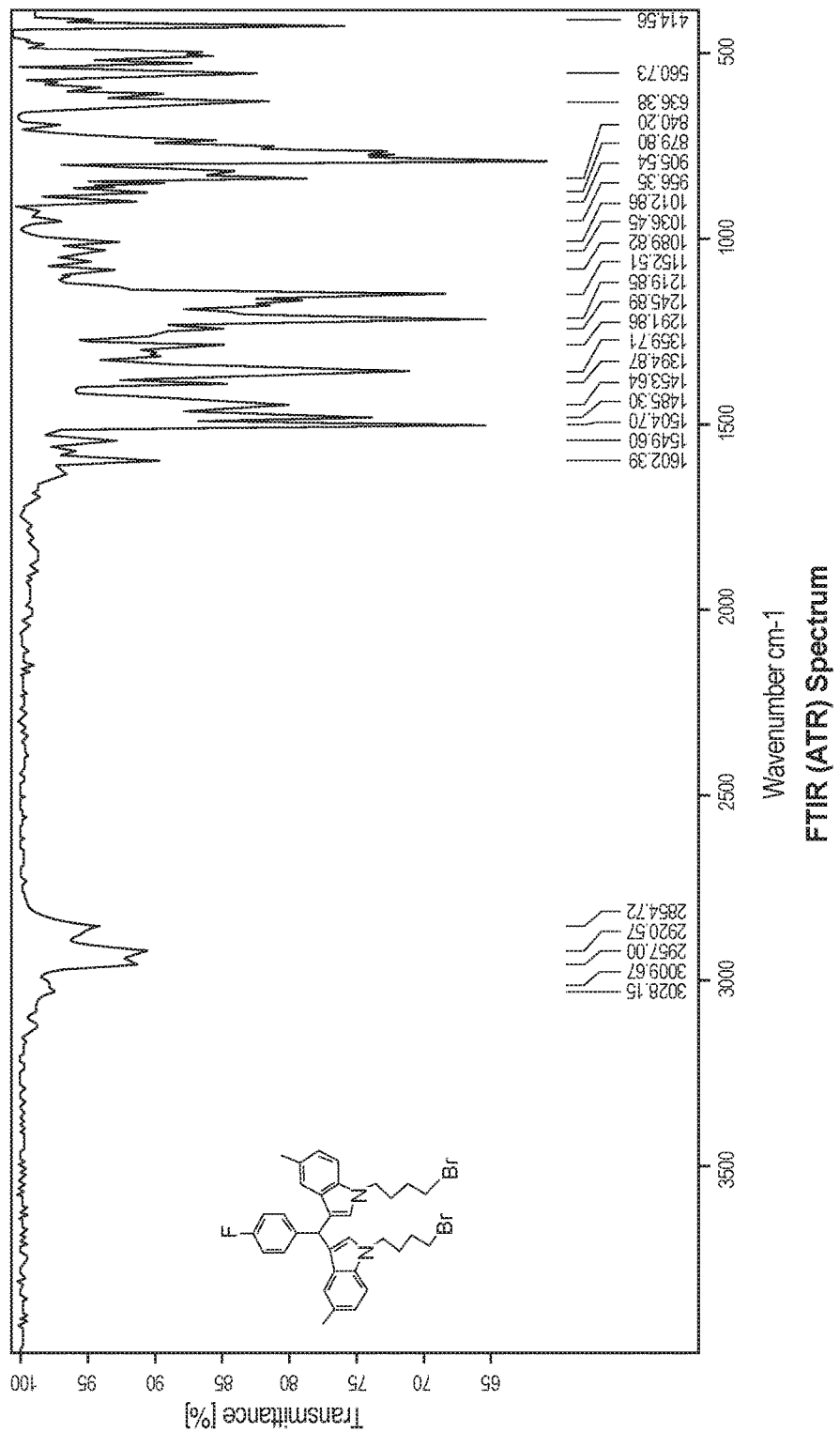
Figure 19:
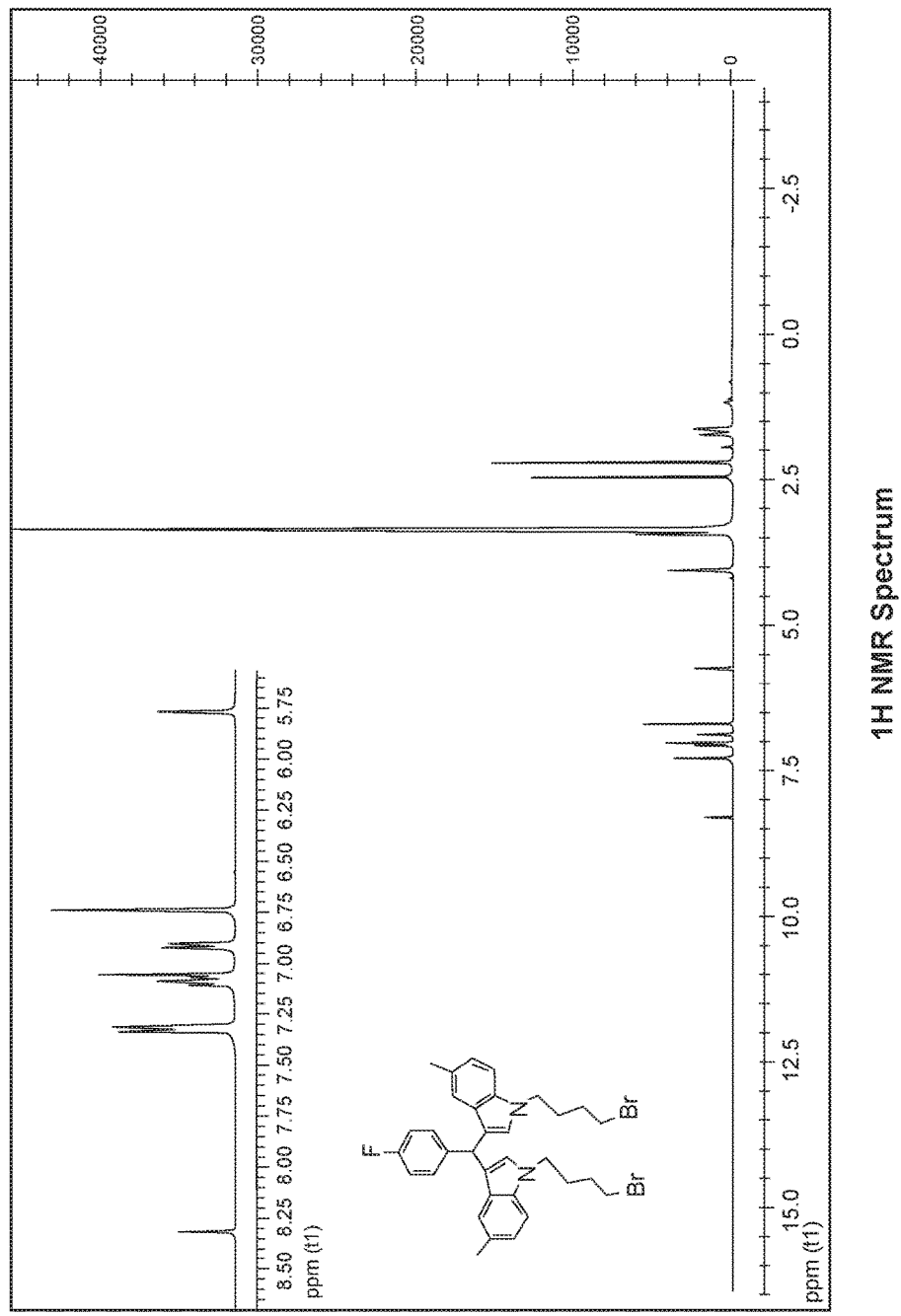
Figure 20:
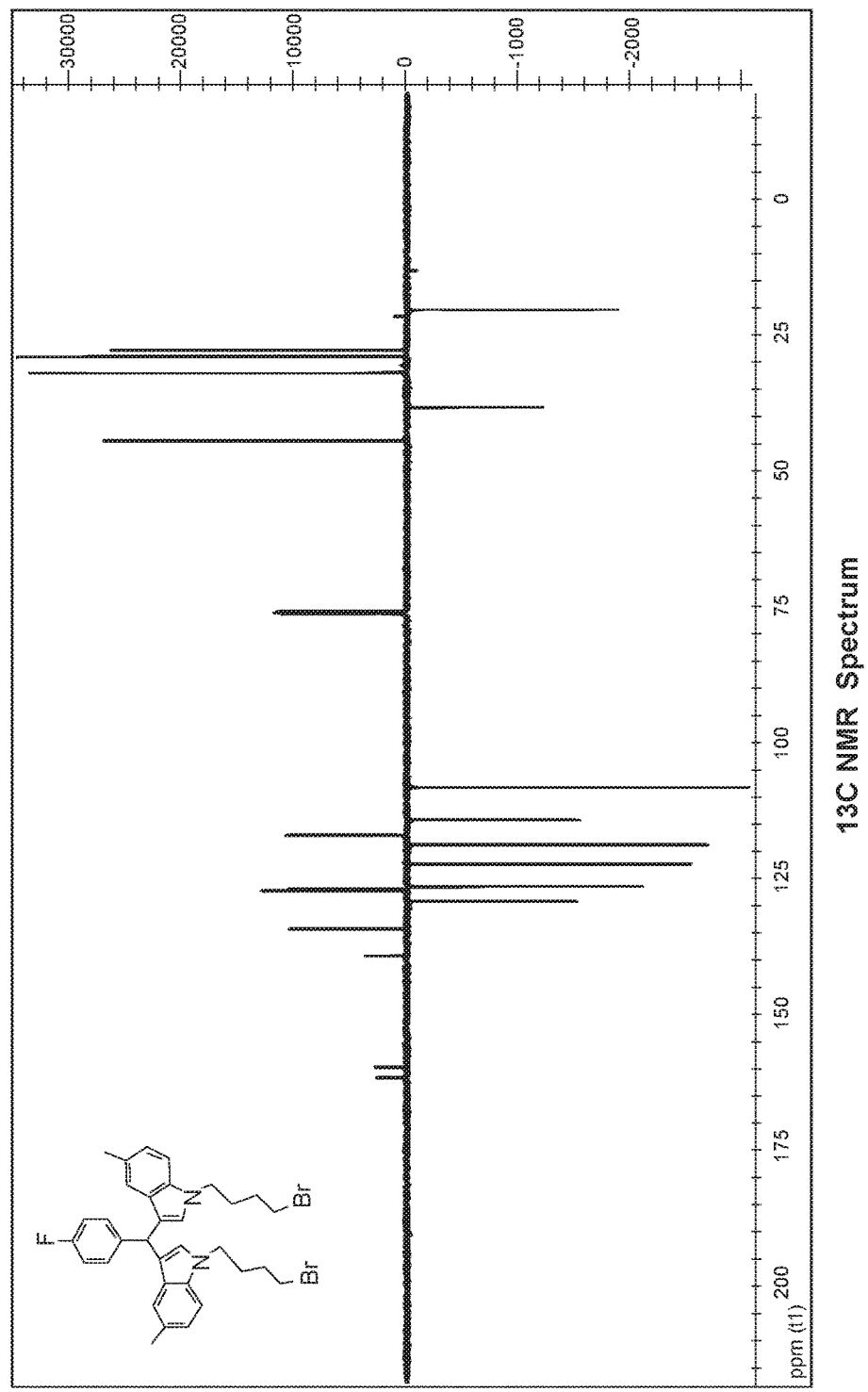
Figure 21:
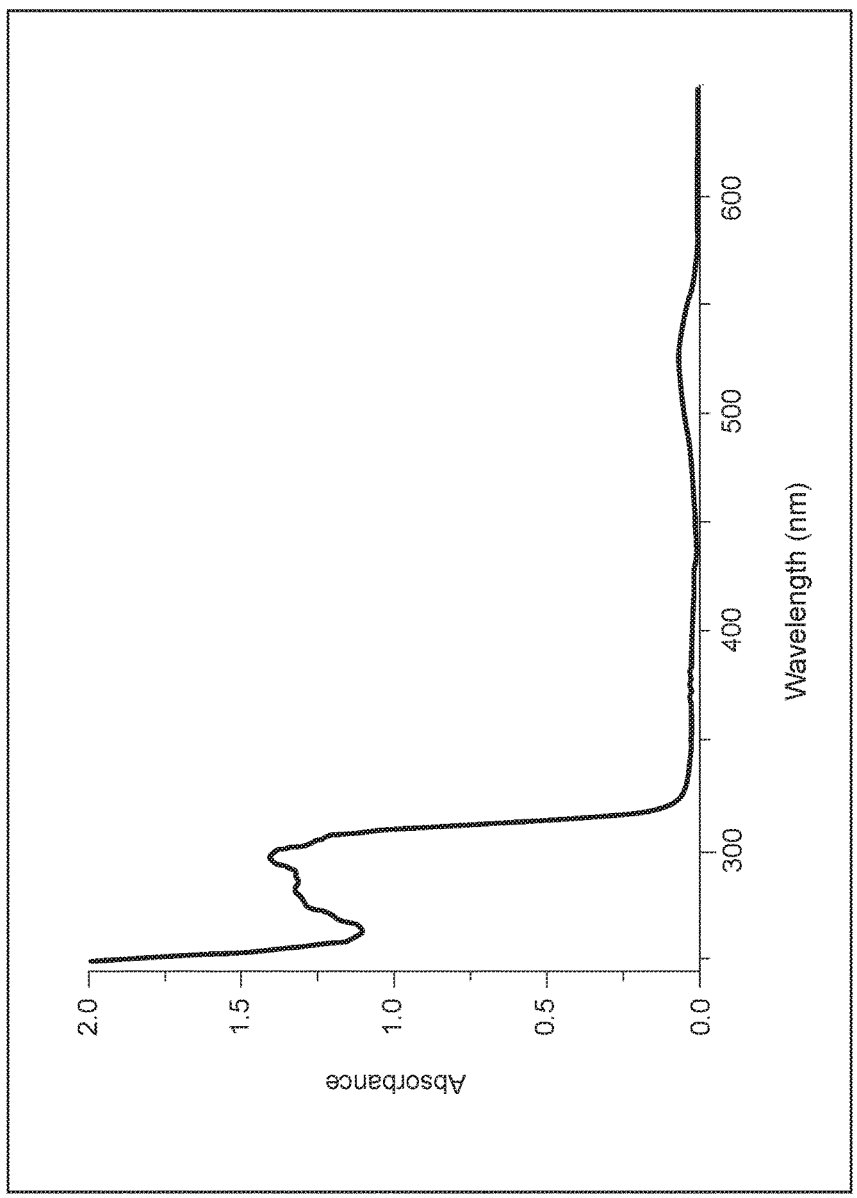
Figure 22:
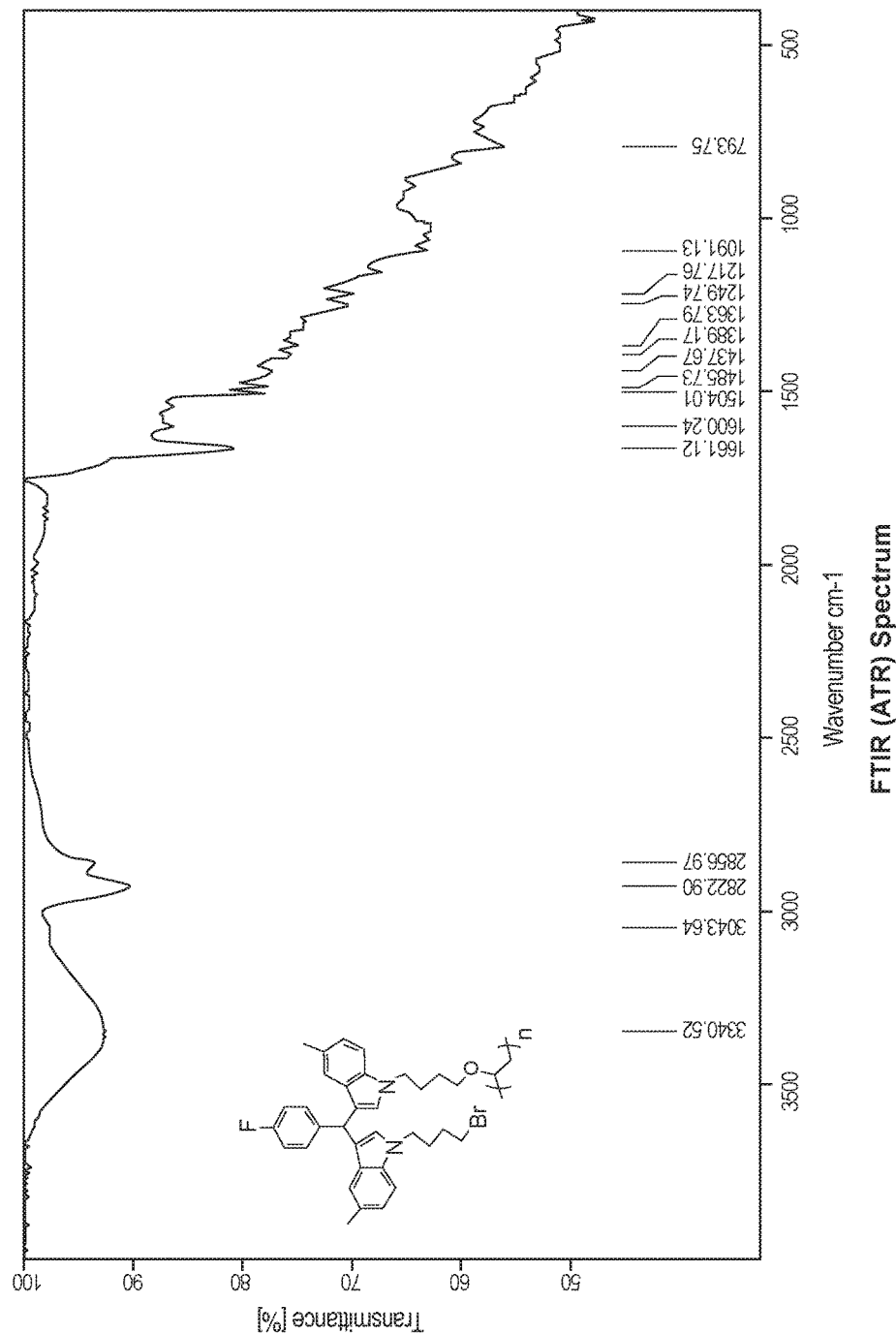
Figure 23:
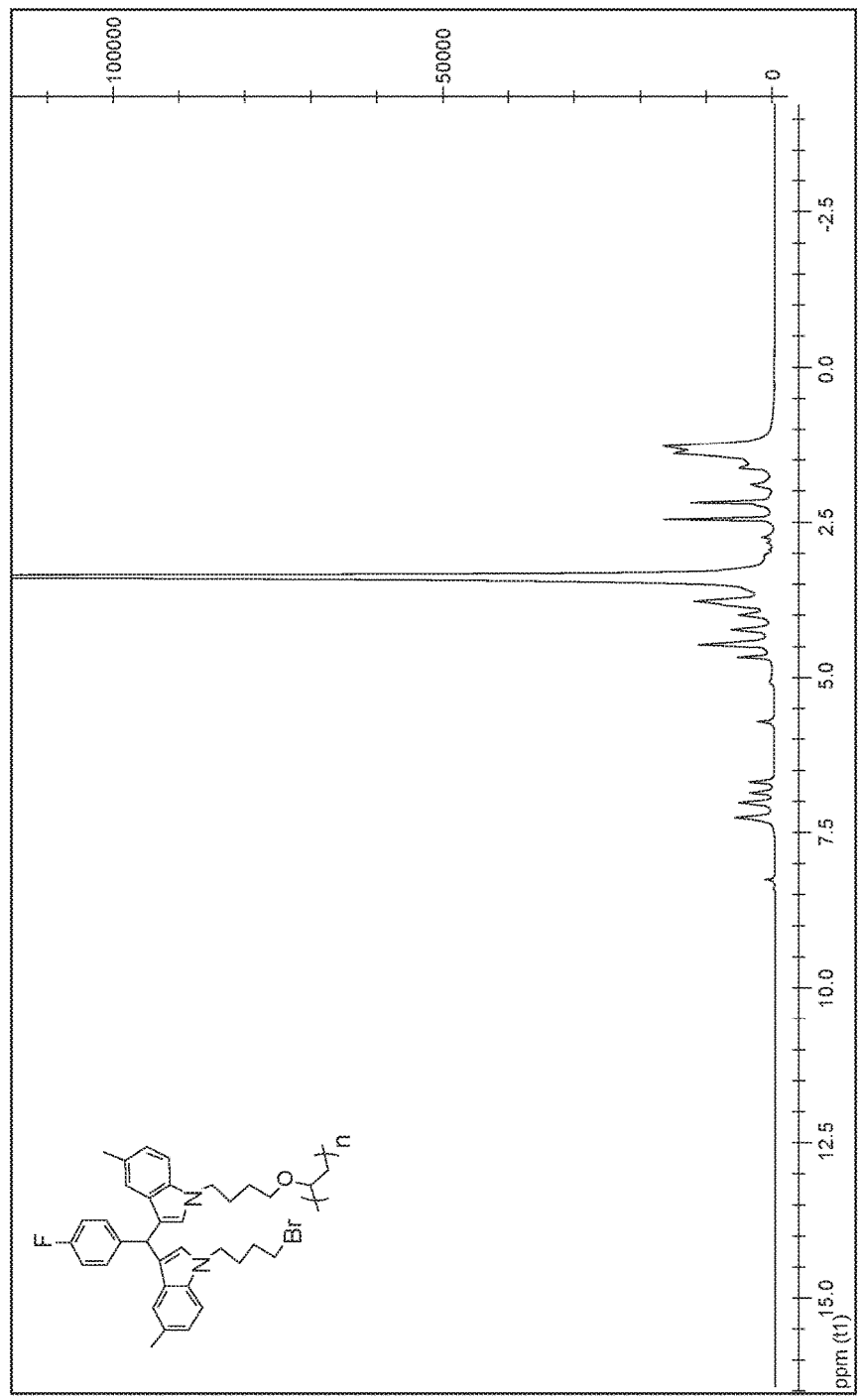
Figure 24:
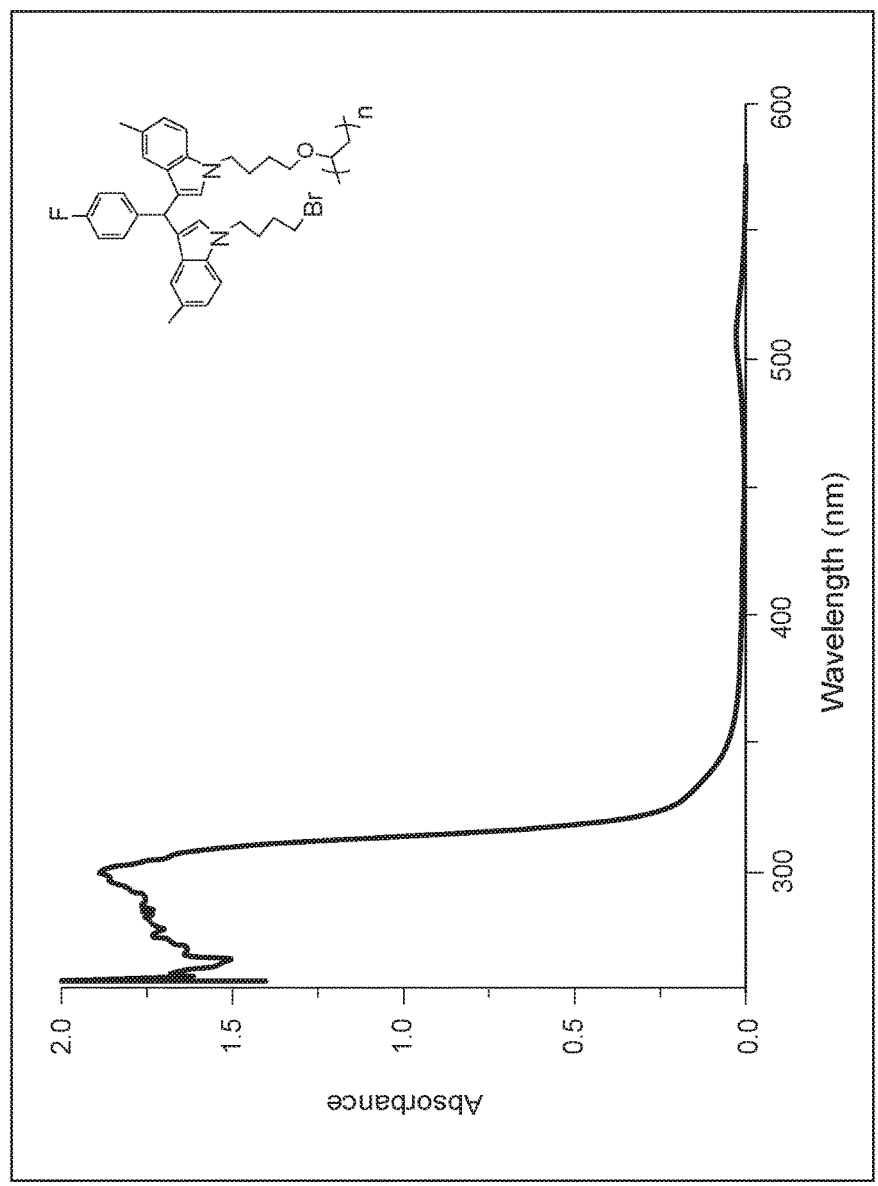

See FIGS. 18 to 24

Example 4

UPF Test
AATCC 183-2004 Method

The transmission of ultraviolet radiation (UV-R) through a specimen is measured on a spectrophotometer at known wavelength intervals. The ultraviolet protection factor (UPF) is computed as the ratio of the erythemally weighted ultraviolet radiation (UV-R) irradiance at the detector with no specimen to the erythemally weighted UV-R irradiance at the detector with a specimen present.

The erythemally weighted UV-R irradiance at the detector with no specimen present is equal to the summation between wavelength intervals of the measured spectral irradiance times the relative spectral effectiveness for the relevant erythemal action spectra times the UV-R weighting function of the appropriate solar radiation spectrum times the appropriate wavelength interval.

The erythemally weighted UV-R irradiance at the detector with a specimen present is equal to the summation between wavelength intervals of the measured spectral irradiance times the relative spectral effectiveness for the relevant erythemal action spectrum times the spectral transmittance for the specimen times the wavelength interval.

The percent blocking of UVA and UVB radiation is also calculated as disclosed in AATCC 183-2004.

Results

Transmittance or Blocking of Erythemally Weighted Ultraviolet Radiation through Fabrics AATCC 183:2014

Conditioning

Prior to testing: 21±1° C. temperature and 65±2% relative humidity

At time of testing: 21° C. temperature and 66% relative humidity

Ultraviolet protection value for label (According to ASTM D 6603-Unprepared Specimen): 1324

Protection Classification: Excellent UV-protection category to UPF Value 40 or greater.

The results are reported in the Figures, wherein

FIG. 25 shows the results on a sample of a non treated ecru woven fabric.

FIG. 26 shows the results on a sample of a light pink woven swatch treated with the compound of Example 1;

FIG. 27 shows the results on a sample of a light pink woven swatch treated with the compound of Example 2;

FIG. 28 shows the results on a sample of a pink woven swatch treated with the compound of Example 3;

As it can be seen from the data reported in the enclosed Figures, the treated samples showed excellent UV-protection, while the non-treated sample did not.

Example 5

Antimicrobial Test

Antibacterial tests were carried out using Washing Standart: BS EN ISO 6330 5A, and Antibacterial Test Standart: AATCC 147:2011.

The results are reported herein below.

| Inhibition zone mm mean value | Bacteria Growth | Assessment |
|---|---|---|
| >1 | None | Good effect |
| 0-1 | | |
| 0 | | |
| 0 | Slight | Limit of Efficacy |
| 0 | Moderate heavy | Insufficient effect |
| 0 | | |

Test on a Sample of a Yellow Printed Woven Fabric Treated with the Compound of Example 1

| Inhibition Zone mm [1] | Bacteria Growth [2] |
|---|---|
| 0 | (-) |

(-) no bacterial colonies directly under the treated sample in the contact area were observed. Inhibition zone exists—Good Effect
[1] Width of clear zone of inhibition in mm
[2] (-) no bacterial colonies directly under the treated sample

| Microorganism | Staphylococcus aureus ATCC 6538 Gram (+) |
|---|---|
| Size of sample | 25 × 50 mm |
| Incubation Temperature | 37° C.±2° C. |
| Incubation time | 18-24 hrs |
| Number of washing | — |
| Washing method | — |

Test on a Sample of a Pink Woven Fabric Treated with the Compound of Example 2

| Inhibition Zone mm [1] | Bacteria Growth [2] |
|---|---|
| 0 | (-) |

(-) no bacterial colonies directly under the treated sample in the contact area were observed. Inhibition zone exists—Good Effect
[3] Width of clear zone of inhibition in mm
[4] (-) no bacterial colonies directly under the treated sample

| Microorganism | Staphylococcus aureus ATCC 6538 Gram (+) |
|---|---|
| Size of sample | 25 × 50 mm |
| Incubation Temperature | 37° C.±2° C. |
| Incubation time | 18-24 hrs |
| Number of washing | — |
| Washing method | — |

Test on a Sample of a Pink Woven Fabric Treated with the Compound of Example 3

| Inhibition Zone mm [1] | Bacteria Growth [2] |
|---|---|
| 0 | (-) |

(-) no bacterial colonies directly under the treated sample in the contact area were observed. Inhibition zone exists—Good Effect
[5] Width of clear zone of inhibition in mm
[6] (-) no bacterial colonies directly under the treated sample

| Microorganism | Staphylococcus aureus ATCC 6538 Gram (+) |
|---|---|
| Size of sample | 25 × 50 mm |
| Incubation Temperature | 37° C.±2° C. |
| Incubation time | 18-24 hrs |
| Number of washing | — |
| Washing method | — |

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A compound of formula (I)

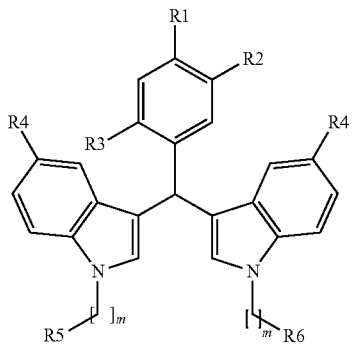

wherein:

- $R_1$ is selected from the group consisting of hydrogen, a halogen atom, a non-substituted, saturated or unsaturated, linear or branched, acyclic C1-C10 alkyl group; and a non-substituted, saturated or unsaturated, linear or branched, acyclic C1-C10 alkoxy group; when $R_2$ and $R_3$ are H;
- $R_2$ is selected from the group consisting of hydrogen, a non-substituted, saturated or unsaturated, linear or branched, acyclic C1-C10 alkyl group, and a non-substituted, saturated or unsaturated, linear or branched, acyclic C1-C10 alkoxy group; when $R_1$ is H and $R_3$ are alkyl or alkoxy groups as above defined;
- $R_3$ is selected from the group consisting of hydrogen, a halogen atom, a non-substituted, saturated or unsaturated, linear or branched, acyclic C1-C10 alkyl group, and a non-substituted, saturated or unsaturated, linear or branched, acyclic C1-C10 alkoxy group; when $R_1$ is H and $R_3$ are halogen, alkyl or alkoxy as above defined;
- $R_4$ is selected from the group consisting of a non-substituted, saturated or unsaturated, linear or branched, acyclic C1-C10 alkyl group, and a non-substituted, saturated or unsaturated, linear or branched, acyclic C1-C10 alkoxy group;
- $R_5$ is selected from a halogen atom; polyvinylalcohol; polyvinylamine and a cellulose-polymer;
- $R_6$ is selected from the group consisting of a halogen atom; polyvinylalcohol; polyvinylamine and a cellulose-polymer; and
- m is from 3 to 5.

2. The compound according to claim 1, wherein said $R_2$ is hydrogen; said $R_1$ and said $R_3$ are both chlorine; said $R_4$ and said $R_5$ are both methyl groups; said $R_5$ and said $R_6$ are both bromine and m is 4.

3. The compound according to claim 1, wherein said $R_1$ is hydrogen; said $R_2$ and said $R_3$ are both a methoxy group; each said $R_4$ is a methyl group; said $R_5$ and said $R_6$ are both bromine and m is 4.

4. The compound according to claim 1, wherein said $R_1$ is fluorine; said $R_2$ and said $R_3$ are both hydrogen; each said $R_4$ is a methyl group; said $R_5$ and said $R_6$ are both bromine and m is 4.

5. The compound according to claim 1, wherein said $R_2$ is hydrogen; said $R_1$ and said $R_1$ are both chlorine; said $R_4$s are methyl groups; said $R_5$ is bromine and said $R_6$ is polyvinylalcol and m is 4.

6. The compound according to claim 1, wherein said $R_1$ is hydrogen; said $R_2$ and said $R_3$ are both a methoxy group; each said $R_4$ is a methyl group; said $R_5$ is bromine and said $R_6$ is polyvinylalcol and m is 4.

7. The compound according to claim 1, wherein said $R_1$ is fluorine; said $R_2$ and said $R_3$ are both hydrogen; each said $R_4$ is a methyl group; said $R_5$ is bromine and said $R_6$ is polyvinylalcol and m is 4.

8. The compound according to claim 1, wherein said PVA molecular weight is approx. 100,000-130,000 g/mol with a Pw: 2,700 (polymerisation degree) and hydrolysis ratio: 86-88%.

9. A method to make fabrics that are sun-protective and anti-infective fabrics, said method comprising treating said fabrics with at least a compound according to claim 1.

10. A fabric comprising clothing or a Personal Protective Equipment (PPE) treated with at least one compound according to claim 1.

11. A process for the preparation of a compound according to claim 1, the process comprising reacting compounds of formula (II) and (III) according to the following scheme

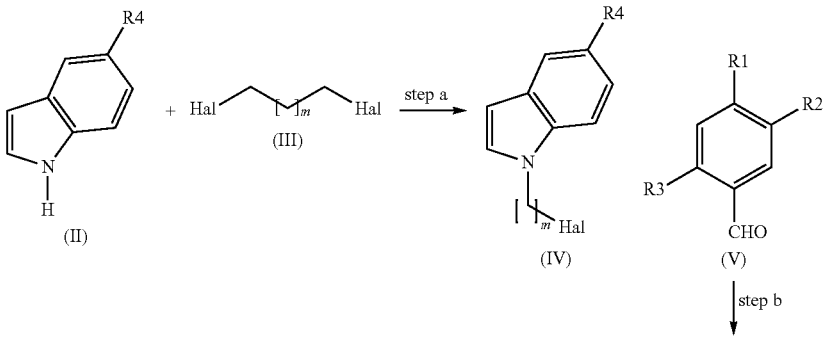

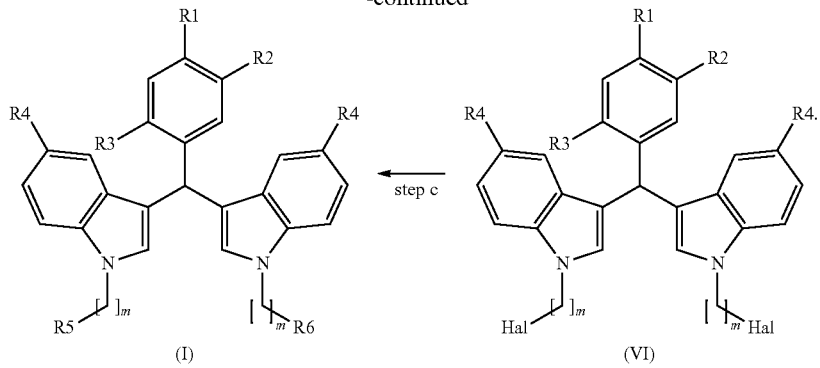

12. The process of claim 11, wherein, in said step a, a compound of formula (II) is reacted with a compound of formula (III) in an appropriate solvent, in the presence of a strong base, the molar ratio compound (II)/compound (III)/base being about 1/4/2.

13. The process of claim 11, wherein, in step b, a compound of formula (IV) is reacted with benzaldehyde of formula (V), in a molar ratio of at least 2/1, in the presence of catalytic amounts of 1,3-dibromo-5,5-dimethylhidantoin (DBDMH), without the presence of any solvent.

14. The process of claim 11, wherein, in step c, a compound (VI) is reacted with a reactant selected from the group consisting of polyvinylalcohol; polyvinylamine and a cellulose-polymer, in a suitable solvent and in the presence of a base.

15. The process of claim 11, wherein said Hal is bromine, and said $R_4$ is methyl.

16. The process of claim 11, wherein said $R_5$ is bromine and said $R_6$ is polyvinylalcohol (PVA).

17. The method according to claim 9, wherein said fabrics are cotton fabrics.

18. The method according to claim 9, wherein said fabrics are denim fabrics.

* * * * *